United States Patent
Muranaka et al.

(10) Patent No.: US 9,193,980 B2
(45) Date of Patent: Nov. 24, 2015

(54) **TRITERPENE OXIDASE DERIVED FROM PLANT BELONGING TO GENUS *GLYCYRRHIZA*, GENE ENCODING THE SAME, AND METHOD OF USING THE SAME**

(75) Inventors: Toshiya Muranaka, Kanagawa (JP); Hikaru Seki, Kanagawa (JP); Kiyoshi Ohyama, Kanagawa (JP); Hiroshi Sudo, Chiba (JP); Satoru Sawai, Chiba (JP); Kazuki Saito, Chiba (JP)

(73) Assignee: RIKEN, Wako-shi (JP)

( * ) Notice: Subject to any disclaimer, the term of this patent is extended or adjusted under 35 U.S.C. 154(b) by 637 days.

(21) Appl. No.: 13/061,262

(22) PCT Filed: Aug. 31, 2009

(86) PCT No.: PCT/JP2009/065197
§ 371 (c)(1),
(2), (4) Date: Sep. 20, 2011

(87) PCT Pub. No.: WO2010/024437
PCT Pub. Date: Mar. 4, 2010

(65) Prior Publication Data
US 2012/0246760 A1    Sep. 27, 2012

(30) Foreign Application Priority Data

Aug. 29, 2008  (JP) .................................. 2008-222483

(51) Int. Cl.
*A01H 5/00*         (2006.01)
*C07H 21/04*        (2006.01)
*C12N 9/02*         (2006.01)
*C12N 15/63*        (2006.01)
*C12P 7/40*         (2006.01)
*C12N 9/04*         (2006.01)
*C12P 33/00*        (2006.01)

(52) U.S. Cl.
CPC ................. *C12P 7/40* (2013.01); *C12N 9/0006* (2013.01); *C12P 33/00* (2013.01)

(58) Field of Classification Search
None
See application file for complete search history.

(56) References Cited

U.S. PATENT DOCUMENTS

2003/0177518 A1   9/2003  Osbourn et al.
2004/0002105 A1   1/2004  Dixon et al.

FOREIGN PATENT DOCUMENTS

JP      2005-137291       6/2005
WO      2003 093428      11/2003
WO   WO 2005/080572 A1    9/2005

OTHER PUBLICATIONS

Seki et al, 2011, Plant Cell, 23:4112-4123.*
Li et al, 2007, Planta, 226:109-123.*
Extended European Search Report issued Jul. 3, 2012 in European Patent Application No. 09810081.1.
Extended European Search Report issued Jan. 20, 2012 in European Patent Application No. 08792426.2.
Hikaru Seki, et al., "Triterpene Functional Genomics in Licorice for Identification of CYP72A154 Involved in the Biosynthesis of Glycyrrhizin", The Plant Cell, vol. 23, No. 11, XP 002677792, Nov. 2011, pp. 4112-4123.
Pimpimon Tansakul, et al., "Dammarenediol-II synthase, the first dedicated enzyme for ginsenoside biosynthesis, in *Panax ginseng*", FEBS Letters, vol. 580, No. 22, XP025232563, Oct. 2, 2006, pp. 5143-5149.
Hiroaki Hayashi, et al., "Cloning and Characterization of a cDNA Encoding β-Amyrin Synthase Involved in Glycyrrhizin and Soyasaponin Biosyntheses in Licorice", Biological & Pharmaceutical Bulletin, vol. 24, No. 8, XP002978733, Aug. 1, 2001, pp. 912-916.
Li, L., et al., "Genome-wide identification and characterization of putative cytochrome P450 genes in the model legume *Medicago truncatula*," Planta, vol. 226, pp. 109-123, (Feb. 2, 2007).
Nomura, T., et al., "Cytochrome P450s in plant steroid hormone synthesis and metabolism," Phytochem Rev., vol. 5, pp. 421-432, (Nov. 15, 2006).
Shibuya, M., et al., "Identification of β-amyrin and sophoradiol 24-hydroxylase by expressed sequence tag mining and functional expression assay," FEBS Journal, vol. 273, pp. 948-959, (2006).
Seki, H., et al., "Licorice β-amyrin 11-oxidase, a cytochrome P450 with a key role in the biosynthesis of the triterpene sweetener glycyrrhizin," PNAS, vol. 105, No. 37, pp. 14204-14209, (Sep. 16, 2008).
International Search Report issued Nov. 24, 2009 in PCT/JP09/065197 filed Aug. 31, 2009.
Iddo Friedberg, "Automated protein function prediction—the genomic challenge", Briefings in Bioinformatics, vol. 7, No. 3, 2006, pp. 225-242.
Akira Ikuta, "The Triterpenes from *Stauntonia Hexaphylla* Callus Tissues and their Biosynthetic Significance", Journal of Natural Products, vol. 52, No. 3, 1989, pp. 623-628.
Hideyuki Suzuki, et al., "A genomics approach to the early stages of triterpene saponin biosynthesis in *Medicago truncatula*", The Plant Journal, vol. 32, 2002, pp. 1033-1048.
D. A. H. Taylor, "Triterpenes from *Salvia glutinosa* L.", J. Chem. Soc. (C), 1967, p. 490.
Arifa Ahamed, et al., "An Artificial Sweetener Stimulates the Sweet Taste in Insect: Dual Effects of Glycyrrhizin in *Phormia regina*", Chem. Senses, vol. 26, 2001, pp. 507-515.
Office Action as received in the corresponding Japanese Patent Application No. 2010-526810 dated Sep. 24, 2014.

* cited by examiner

*Primary Examiner* — David H Kruse
*Assistant Examiner* — Jason Deveau Rosen
(74) *Attorney, Agent, or Firm* — Oblon, McClelland, Maier & Neustadt, L.L.P.

(57) ABSTRACT

Identification of a protein having an activity of oxidizing oleanane-type triterpene, and a gene encoding the protein, the protein and the gene, and use thereof are provided. For example, a protein having an activity of oxidizing oleanane-type triterpene obtained from a plant in the family Fabaceae, a gene encoding the protein and use thereof are provided. The protein is shown in, for example, SEQ ID NO: 4, 14 or 18, and the gene encoding the protein is shown in, for example, SEQ ID NO: 3, 13 or 17. A transformant into which the gene is introduced can be produced, and thereby a triterpene oxidase can be obtained.

25 Claims, 12 Drawing Sheets

SEQUENCE LISTING

<160> NUMBER OF SEQ ID NOS: 20

<210> SEQ ID NO 1
<211> LENGTH: 26
<212> TYPE: DNA
<213> ORGANISM: Artificial
<220> FEATURE:
<223> OTHER INFORMATION: primer

<400> SEQUENCE: 1
caccatggat gcatcttcca caccag          26

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
ttacagttta tgcagaatga tgggtgcc        28

<210> SEQ ID NO 3
<211> LENGTH: 1572
<212> TYPE: DNA
<213> ORGANISM: Glycyrrhiza uralensis

<400> SEQUENCE: 3
atggatgcat cttccacacc aggggctatc tgggttgttc tgacagtgat actagctgcg    60
attcccatat gggtatgcca tatggtgaac acgctgtggc tgaggccaaa gaggttggaa    120
aggcatctca gagctcaagg tcttcatggc gacccttaca agctctcact tgacaactcc    180
aagcaaacct atatgctcaa gttgcaacaa gaagcacaat caaaatccat tggtctctcc    240
aaagatgatg ctgcaccacg aatcttctcc cttgcccatc aaactgtaca caaatatgga    300
aagaactcct ttgcatggga agggacagca ccaaaggtga tcatcacaga cccagagcaa    360
attaaggaag tctttaacaa gattcaggac ttccccaaac caaaattaaa tcccatcgcc    420
aagtatatta gcatcggtct agtacagtat gagggtgaca aatgggccaa acatcgaaag    480
attatcaatc cggcattcca cttagaaaaa ttgaaaggta tgctgccagc attttctcat    540
agctgccatg aaatgattag caaatggaag gggttattgt catcagatgg aacatgtgag    600
gttgatgttt ggcccttcct tcaaaatctc acttgtgatg taatttctag gacggcattc    660
ggaagcagct atgcagaagg agcaaaaata tttgaacttt gaaaaggca gggatatgct    720 ttgatgacag cacgatacgc acgcattcca ttatggtggc ttctaccatc aactaccaaa    780
aggaggatga aggaaattga agaggcata cgtgattcac ttgaaggtat cattagaaaa    840
cgagaaaaag cattgaagag tggcaaaagc accgatgacg acttattagg catacttttg    900
caatcaaatc acattgaaaa taaggagat gaaaacagta agagtgctgg aatgaccacc    960
caagaagtaa tggaggaatg caaactttt tacctggcag ggcaagagac caccgcggct   1020
ttgctggcct ggacaatggt gttattaggc aagcatcctg aatggcaagc acgtgcaagg   1080
caggaagttt tgcaagtttt tgggaatcaa aatccaaact tcgaagggtt aggtcgcctc   1140

```
aaaattgtaa ccatgatttt atatgaggta ctcaggctgt acccacctgg gatttacctc      1200
acccgagctc ttcgaaagga tttgaaactt ggaaacettt tgctacctgc tggagtacag      1260
gtttccgtac caatactttt gattcaccat gatgaaggta tatggggcaa tgatgcaaag      1320
gagttcaatc ctgaaaggtt tgctgaagga attgcaaagg caacaaaagg ccaagtttgc      1380
tatttccctt ttggatgggg tcctagaata tgtgttgggc aaaactttgc cttattagaa      1440
gccaagattg tattgtcatt gctgctgcag aatttctcat ttgagctatc tccgacttat      1500
gcacatgttc ctaccacggt gcttactttg cagccaaaac atggggcacc catcattctg      1560
cataaactgt aa                                                         1572
```

<210> SEQ ID NO 4
<211> LENGTH: 523
<212> TYPE: PRT
<213> ORGANISM: Glycyrrhiza uralensis

<400> SEQUENCE: 4

```
Met Asp Ala Ser Ser Thr Pro Gly Ala Ile Trp Val Val Leu Thr Val
 1               5                   10                  15

Ile Leu Ala Ala Ile Pro Ile Trp Val Cys His Met Val Asn Thr Leu
            20                  25                  30

Trp Leu Arg Pro Lys Arg Leu Glu Arg His Leu Arg Ala Gln Gly Leu
        35                  40                  45

His Gly Asp Pro Tyr Lys Leu Ser Leu Asp Asn Ser Lys Gln Thr Tyr
    50                  55                  60

Met Leu Lys Leu Gln Gln Glu Ala Gln Ser Lys Ser Ile Gly Leu Ser
65                  70                  75                  80

Lys Asp Asp Ala Ala Pro Arg Ile Phe Ser Leu Ala His Gln Thr Val
                85                  90                  95

His Lys Tyr Gly Lys Asn Ser Phe Ala Trp Glu Gly Thr Ala Pro Lys
           100                 105                 110

Val Ile Ile Thr Asp Pro Glu Gln Ile Lys Glu Val Phe Asn Lys Ile
       115                 120                 125

Gln Asp Phe Pro Lys Pro Lys Leu Asn Pro Ile Ala Lys Tyr Ile Ser
   130                 135                 140

Ile Gly Leu Val Gln Tyr Glu Gly Asp Lys Trp Ala Lys His Arg Lys
145                 150                 155                 160

Ile Ile Asn Pro Ala Phe His Leu Glu Lys Leu Lys Gly Met Leu Pro
                165                 170                 175

Ala Phe Ser His Ser Cys His Glu Met Ile Ser Lys Trp Lys Gly Leu
           180                 185                 190

Leu Ser Ser Asp Gly Thr Cys Glu Val Asp Val Trp Pro Phe Leu Gln
       195                 200                 205

Asn Leu Thr Cys Asp Val Ile Ser Arg Thr Ala Phe Gly Ser Ser Tyr
   210                 215                 220

Ala Glu Gly Ala Lys Ile Phe Glu Leu Leu Arg Gln Gly Tyr Ala
225                 230                 235                 240

Leu Met Thr Ala Arg Tyr Ala Arg Ile Pro Leu Trp Trp Leu Leu Pro
                245                 250                 255

Ser Thr Thr Lys Arg Arg Met Lys Glu Ile Glu Arg Gly Ile Arg Asp
           260                 265                 270

Ser Leu Glu Gly Ile Ile Arg Lys Arg Glu Lys Ala Leu Lys Ser Gly
       275                 280                 285
```

```
Lys Ser Thr Asp Asp Asp Leu Leu Gly Ile Leu Leu Gln Ser Asn His
        290                 295                 300

Ile Glu Asn Lys Gly Asp Glu Asn Ser Lys Ser Ala Gly Met Thr Thr
305                 310                 315                 320

Gln Glu Val Met Glu Glu Cys Lys Leu Phe Tyr Leu Ala Gly Gln Glu
                325                 330                 335

Thr Thr Ala Ala Leu Leu Ala Trp Thr Met Val Leu Leu Gly Lys His
                340                 345                 350

Pro Glu Trp Gln Ala Arg Ala Arg Gln Glu Val Leu Gln Val Phe Gly
            355                 360                 365

Asn Gln Asn Pro Asn Phe Glu Gly Leu Gly Arg Leu Lys Ile Val Thr
370                 375                 380

Met Ile Leu Tyr Glu Val Leu Arg Leu Tyr Pro Pro Gly Ile Tyr Leu
385                 390                 395                 400

Thr Arg Ala Leu Arg Lys Asp Leu Lys Leu Gly Asn Leu Leu Leu Pro
                405                 410                 415

Ala Gly Val Gln Val Ser Val Pro Ile Leu Leu Ile His His Asp Glu
                420                 425                 430

Gly Ile Trp Gly Asn Asp Ala Lys Glu Phe Asn Pro Glu Arg Phe Ala
            435                 440                 445

Glu Gly Ile Ala Lys Ala Thr Lys Gly Gln Val Cys Tyr Phe Pro Phe
450                 455                 460

Gly Trp Gly Pro Arg Ile Cys Val Gly Gln Asn Phe Ala Leu Leu Glu
465                 470                 475                 480

Ala Lys Ile Val Leu Ser Leu Leu Leu Gln Asn Phe Ser Phe Glu Leu
                485                 490                 495

Ser Pro Thr Tyr Ala His Val Pro Thr Thr Val Leu Thr Leu Gln Pro
                500                 505                 510

Lys His Gly Ala Pro Ile Ile Leu His Lys Leu
            515                 520

<210> SEQ ID NO 5
<211> LENGTH: 45
<212> TYPE: DNA
<213> ORGANISM: Artificial
<220> FEATURE:
<223> OTHER INFORMATION: primer

<400> SEQUENCE: 5
ggatgatcca ctagtggatc ctctagctcc ctaacatgta ggtgg            45

<210> SEQ ID NO 6
<211> LENGTH: 45
<212> TYPE: DNA
<213> ORGANISM: Artificial
<220> FEATURE:
<223> OTHER INFORMATION: primer

<400> SEQUENCE: 6
taatgcaggg ccgcaggatc cgtgtggaag aacgattaca acagg            45

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
```
tgcggccctg cattaatgaa tcggccaacg                                       30

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
actagtggat catccccacg cgccctgtag                                       30

<210> SEQ ID NO 9
<211> LENGTH: 44
<212> TYPE: DNA
<213> ORGANISM: Artificial
<220> FEATURE:
<223> OTHER INFORMATION: primer

<400> SEQUENCE: 9
gggcggccgc actagtatcg atggaagaat caagctccat gaag                       44

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
ttaattaatc accatacatc acgcaaatac                                       30

<210> SEQ ID NO 11
<211> LENGTH: 40
<212> TYPE: DNA
<213> ORGANISM: Artificial
<220> FEATURE:
<223> OTHER INFORMATION: primer

<400> SEQUENCE: 11
cgccggatcc accatggaag tacattgggt ttgcatgtcc                            40

<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12
gccctctaga ctaagcacat gaaaccttta tcaccttagc                            40

<210> SEQ ID NO 13
<211> LENGTH: 1572
<212> TYPE: DNA
<213> ORGANISM: Glycyrrhiza glabra

<400> SEQUENCE: 13
atggatgcat cttccacacc agggctatc tggttgttc taacagtgat actagctgcg        60
attcccatat gggcatgcca tatggtcaac acgctgtggc tgaggccaaa gaggttggaa     120
aggcatctca gagctcaagg tcttcatggt gacccttaca agctctcact tgacaactcc     180
aagcaaatct atatgctcaa gttgcaacaa gaagcacaat caaatccat tggtctctcc     240 aaagatgatg ctgcaccacg aatcttctcc cttgcccatc aaactgtaca caaatatgga     300

```
aagaactcct ttgcatggga agggacaaca ccaaaggtga tcatcacaga cccagagcaa    360
attaaggaag tctttaacaa gattcaggac ttccccaaac caaaattaaa tcccatcgcc    420
aagtatatta gcatcggtct agtacattat gagggtgaca atgggccaa acatcgaaag     480 attatcaatc cggcattcca cttagaaaaa ttgaaaggta tgctgccagc attttctcat    540
agctgccatg aaatgattag caaatggaag gggttattgt cagtagatgg aacgtgtgag    600
gttgatgttt ggccccttcct tcaaaatctc acttgtgatg taatttctag dacggcattc   660
ggaagcagct atgcagaagg agcaataata tttgaacttt tgaaaaggca gggatatgct    720
ttgatgacag cacgatacgc gcgcattcca ttatggtggc ttctaccatc aactaccaaa    780
aggaggatga aggaaattga agaggcata cgtgattcac ttgaaggtat cattagaaaa     840
cgagaaaaag cattgaagag tggcaaaagc accgatgacg acttattagg catacttttg    900
caatcaaatc acattgaaaa taaggagat gaaaacagta agagtgctgg aatgaccacc     960
caagaagtaa tggaggaatg caaacttttt tacctggcag gcaagagac caccgcggct    1020 ttgctggcct ggacaatggt gttattaggc aagcatcctg aatggcaagc acgtgcaagg   1080
caggaagttt tgcaagtttt tgggaatcaa aatccaaact cgaagggtt aggtcgcctc    1140 aaaattgtaa ccatgattt atatgaggta ctcaggctgt acccacctgg gatttacctc    1200
acccgagctc ttcaaaagga tttgaaactt ggaaaccttt tgctacctgc tggagtacag   1260
gtttccgtac caatactttt gattcaccat gatgaaggta tatggggcaa tgatgcaaag   1320
gagttcaatc ctgaaaggtt tgctgaagga attgcaaagg caacaaaagg ccaagtttgc   1380 tatttcccctt ttggatgggg tcctagaata tgtgttgggc aaaactttgc cttattagaa   1440
gccaagattg tattgtcatt gctgctgcag aatttctcat ttgagttatc tccgagttat   1500
gcacatgttc ctaccacggt gcttactttg cagccaaaac atggggcacc catcattctg   1560
cataaactgt aa                                                       1572
```

<210> SEQ ID NO 14
<211> LENGTH: 523
<212> TYPE: PRT
<213> ORGANISM: Glycyrrhiza glabra

<400> SEQUENCE: 14

```
Met Asp Ala Ser Ser Thr Pro Gly Ala Ile Trp Val Val Leu Thr Val
1               5                   10                  15

Ile Leu Ala Ala Ile Pro Ile Trp Ala Cys His Met Val Asn Thr Leu
            20                  25                  30

Trp Leu Arg Pro Lys Arg Leu Glu Arg His Leu Arg Ala Gln Gly Leu
        35                  40                  45

His Gly Asp Pro Tyr Lys Leu Ser Leu Asp Asn Ser Lys Gln Ile Tyr
    50                  55                  60

Met Leu Lys Leu Gln Gln Glu Ala Gln Ser Lys Ser Ile Gly Leu Ser
65                  70                  75                  80

Lys Asp Asp Ala Ala Pro Arg Ile Phe Ser Leu Ala His Gln Thr Val
                85                  90                  95

His Lys Tyr Gly Lys Asn Ser Phe Ala Trp Glu Gly Thr Thr Pro Lys
            100                 105                 110

Val Ile Ile Thr Asp Pro Glu Gln Ile Lys Glu Val Phe Asn Lys Ile
        115                 120                 125

Gln Asp Phe Pro Lys Pro Lys Leu Asn Pro Ile Ala Lys Tyr Ile Ser
    130                 135                 140
```

-continued

```
Ile Gly Leu Val His Tyr Glu Gly Asp Lys Trp Ala Lys His Arg Lys
145                 150                 155                 160

Ile Ile Asn Pro Ala Phe His Leu Glu Lys Leu Lys Gly Met Leu Pro
            165                 170                 175

Ala Phe Ser His Ser Cys His Glu Met Ile Ser Lys Trp Lys Gly Leu
        180                 185                 190

Leu Ser Val Asp Gly Thr Cys Glu Val Asp Val Trp Pro Phe Leu Gln
    195                 200                 205

Asn Leu Thr Cys Asp Val Ile Ser Arg Thr Ala Phe Gly Ser Ser Tyr
210                 215                 220

Ala Glu Gly Ala Ile Ile Phe Glu Leu Leu Lys Arg Gln Gly Tyr Ala
225                 230                 235                 240

Leu Met Thr Ala Arg Tyr Ala Arg Ile Pro Leu Trp Trp Leu Leu Pro
                245                 250                 255

Ser Thr Thr Lys Arg Arg Met Lys Glu Ile Glu Arg Gly Ile Arg Asp
            260                 265                 270

Ser Leu Glu Gly Ile Ile Arg Lys Arg Glu Lys Ala Leu Lys Ser Gly
        275                 280                 285

Lys Ser Thr Asp Asp Leu Leu Gly Ile Leu Leu Gln Ser Asn His
    290                 295                 300

Ile Glu Asn Lys Gly Asp Glu Asn Ser Lys Ser Ala Gly Met Thr Thr
305                 310                 315                 320

Gln Glu Val Met Glu Glu Cys Lys Leu Phe Tyr Leu Ala Gly Gln Glu
                325                 330                 335

Thr Thr Ala Ala Leu Leu Ala Trp Thr Met Val Leu Leu Gly Lys His
            340                 345                 350

Pro Glu Trp Gln Ala Arg Ala Arg Gln Glu Val Leu Gln Val Phe Gly
        355                 360                 365

Asn Gln Asn Pro Asn Phe Glu Gly Leu Gly Arg Leu Lys Ile Val Thr
    370                 375                 380

Met Ile Leu Tyr Glu Val Leu Arg Leu Tyr Pro Pro Gly Ile Tyr Leu
385                 390                 395                 400

Thr Arg Ala Leu Gln Lys Asp Leu Lys Leu Gly Asn Leu Leu Leu Pro
                405                 410                 415

Ala Gly Val Gln Val Ser Val Pro Ile Leu Leu Ile His His Asp Glu
            420                 425                 430

Gly Ile Trp Gly Asn Asp Ala Lys Glu Phe Asn Pro Glu Arg Phe Ala
        435                 440                 445

Glu Gly Ile Ala Lys Ala Thr Lys Gly Gln Val Cys Tyr Phe Pro Phe
    450                 455                 460

Gly Trp Gly Pro Arg Ile Cys Val Gly Gln Asn Phe Ala Leu Leu Glu
465                 470                 475                 480

Ala Lys Ile Val Leu Ser Leu Leu Leu Gln Asn Phe Ser Phe Glu Leu
                485                 490                 495

Ser Pro Ser Tyr Ala His Val Pro Thr Thr Val Leu Thr Leu Gln Pro
            500                 505                 510

Lys His Gly Ala Pro Ile Ile Leu His Lys Leu
    515                 520
```

<210> SEQ ID NO 15
<211> LENGTH: 1482
<212> TYPE: DNA
<213> ORGANISM: Glycyrrhiza uralensis

<400> SEQUENCE: 15

```
atggaagtac attgggtttg catgtccgct gccactttgt tggtatgcta catttttgga        60
agcaagtttg tgaggaattt gaatgggtgg tattatgatg taaaactaag aaggaaagaa       120
cacccactac ccccaggtga catgggatgg cctcttatcg gcgatctatt gtccttcatc       180
aaagatttct catcgggtca ccctgattca ttcatcaaca accttgttct caaatatgga       240
cgaagtggta tctacaagac tcacttgttt gggaatccaa gcatcattgt ttgtgagcct       300
cagatgtgta ggcgagttct cactgatgat gtgaacttta gcttggtta ccaaaatct        360
atcaaagagt tggcacgatg tagacccatg attgatgtct ctaatgcgga acataggctt       420
tttcgacgcc tcattacttc cccaatcgtg ggtcacaagg cgctagcaat gtacctagag       480
cgtcttgagg aaattgtgat caattcgttg gaagaattgt ccagcatgaa gcaccccgtt       540
gagctcttga agagatgaa gaaggtttcc tttaaagcca ttgtccacgt cttcatgggc        600
tcttccaatc aggacatcat taaaaaaatt ggaagttcgt ttactgattt gtacaatggc       660
atgttctcta tccccattaa cgtacctggt tttacattcc acaaagcact cgaggcacgt       720
aagaagctag ccaaaatagt tcaacccgtt gtggatgaaa ggcggttgat gatagaaaat       780
ggtccacaag aagggagcca agaaaagat cttattgata ttcttttgga agtcaaagat        840
gagaatggac gaaaattgga ggacgaggat attagcgatt tattaatagg cttttgttc        900
gctggccatg aaagtacagc aaccagttta atgtggtcaa ttacgtatct tacacagcat       960
ccccatatct tgaaaaggc taaggaagag caggaagaaa taacgaggac aagattttcc       1020
tcgcagaaac aattaagtct taaggaaatt aagcaaatgg tttatctttc tcaggtaatt      1080
gatgaaactt tacgatgtgc caatattgcc tttgcaactt tcgagaggc aactgctgat       1140
gtgaacatca atggttatat cataccaaag ggatggagag tgctaattg ggcaagagcc       1200
attcatatgg attctgaata ttacccaaat ccagaagaat ttaatccatc gagatgggat      1260
gattacaatg ccaaagcagg aaccttcctt ccttttggag caggaagtag actttgtcct      1320
ggagccgact tggcgaaact tgaaattcc atatttcttc attatttcct ccgtaattac       1380
aggttggaga gaataaatcc agaatgtcac gttaccagct taccagtatc taaacccaca      1440
gacaattgtc tcgctaaggt gataaaggtt tcatgtgctt ag                         1482
```

<210> SEQ ID NO 16
<211> LENGTH: 493
<212> TYPE: PRT
<213> ORGANISM: Glycyrrhiza uralensis

<400> SEQUENCE: 16

```
Met Glu Val His Trp Val Cys Met Ser Ala Ala Thr Leu Leu Val Cys
  1               5                  10                  15

Tyr Ile Phe Gly Ser Lys Phe Val Arg Asn Leu Asn Gly Trp Tyr Tyr
                 20                  25                  30

Asp Val Lys Leu Arg Arg Lys Glu His Pro Leu Pro Pro Gly Asp Met
             35                  40                  45

Gly Trp Pro Leu Ile Gly Asp Leu Leu Ser Phe Ile Lys Asp Phe Ser
         50                  55                  60

Ser Gly His Pro Asp Ser Phe Ile Asn Asn Leu Val Leu Lys Tyr Gly
 65                  70                  75                  80

Arg Ser Gly Ile Tyr Lys Thr His Leu Phe Gly Asn Pro Ser Ile Ile
                 85                  90                  95

Val Cys Glu Pro Gln Met Cys Arg Arg Val Leu Thr Asp Asp Val Asn
```

```
            100                 105                 110
Phe Lys Leu Gly Tyr Pro Lys Ser Ile Lys Glu Leu Ala Arg Cys Arg
            115                 120                 125

Pro Met Ile Asp Val Ser Asn Ala Glu His Arg Leu Phe Arg Arg Leu
            130                 135             140

Ile Thr Ser Pro Ile Val Gly His Lys Ala Leu Ala Met Tyr Leu Glu
145                 150                 155                 160

Arg Leu Glu Glu Ile Val Ile Asn Ser Leu Glu Glu Leu Ser Ser Met
                165                 170                 175

Lys His Pro Val Glu Leu Leu Lys Glu Met Lys Lys Val Ser Phe Lys
            180                 185                 190

Ala Ile Val His Val Phe Met Gly Ser Ser Asn Gln Asp Ile Ile Lys
            195                 200                 205

Lys Ile Gly Ser Ser Phe Thr Asp Leu Tyr Asn Gly Met Phe Ser Ile
            210                 215                 220

Pro Ile Asn Val Pro Gly Phe Thr Phe His Lys Ala Leu Glu Ala Arg
225                 230                 235                 240

Lys Lys Leu Ala Lys Ile Val Gln Pro Val Val Asp Glu Arg Arg Leu
                245                 250                 255

Met Ile Glu Asn Gly Pro Gln Glu Gly Ser Gln Arg Lys Asp Leu Ile
                260                 265                 270

Asp Ile Leu Leu Glu Val Lys Asp Glu Asn Gly Arg Lys Leu Glu Asp
            275                 280                 285

Glu Asp Ile Ser Asp Leu Leu Ile Gly Leu Leu Phe Ala Gly His Glu
            290                 295                 300

Ser Thr Ala Thr Ser Leu Met Trp Ser Ile Thr Tyr Leu Thr Gln His
305                 310                 315                 320

Pro His Ile Leu Lys Lys Ala Lys Glu Glu Gln Glu Glu Ile Thr Arg
                325                 330                 335

Thr Arg Phe Ser Ser Gln Lys Gln Leu Ser Leu Lys Gly Ile Lys Gln
                340                 345                 350

Met Val Tyr Leu Ser Gln Val Ile Asp Glu Thr Leu Arg Cys Ala Asn
            355                 360                 365

Ile Ala Phe Ala Thr Phe Arg Glu Ala Thr Ala Asp Val Asn Ile Asn
            370                 375             380

Gly Tyr Ile Ile Pro Lys Gly Trp Arg Val Leu Ile Trp Ala Arg Ala
385                 390                 395                 400

Ile His Met Asp Ser Glu Tyr Tyr Pro Asn Pro Glu Glu Phe Asn Pro
                405                 410                 415

Ser Arg Trp Asp Asp Tyr Asn Ala Lys Ala Gly Thr Phe Leu Pro Phe
            420                 425                 430

Gly Ala Gly Ser Arg Leu Cys Pro Gly Ala Asp Leu Ala Lys Leu Glu
            435                 440                 445

Ile Ser Ile Phe Leu His Tyr Phe Leu Arg Asn Tyr Arg Leu Glu Arg
            450                 455             460

Ile Asn Pro Glu Cys His Val Thr Ser Leu Pro Val Ser Lys Pro Thr
465                 470                 475                 480

Asp Asn Cys Leu Ala Lys Val Ile Lys Val Ser Cys Ala
                485                 490

<210> SEQ ID NO 17
<211> LENGTH: 1575
<212> TYPE: DNA
<213> ORGANISM: Medigago truncatula
```

<400> SEQUENCE: 17

```
atggaagtgt ttatgtttcc cacaggaaca acagtaatca tctctgttct ttcagttcta        60
cttgctgtga ttccatggta tcttctcaac aagttatggc ttaagccaaa gaggtttgag       120
aaacttctca agctcaagg ttttcaaggt gaaccttata cctttcagt attaaaggac         180
aaatcaaaac aaaattatat gttgaagttg caacaagaag ataaatctaa atccattggt       240
ctctccaaag aagctgcacc gtctatcttc actcctgttc atcaaactgt acgcaaatat       300
ggaaacaatt ccttttatg ggaaggtaca acaccaaggg ttatcatcac agaccctgat        360
caaattaagg atgtatttaa caagattgat gacttcccca aaccaaaact aagatccatc      420
gccaagtatt tgagcgttgg tatactagat catgagggta agaaatgggc taaacatagg      480
aagatcgcca atccagcatt ccacctagaa aaattgaaag ttatgctgcc tgcattttct      540
cacagttgca atgaaatgat aagcaaatgg aaggaactat tgtcatcaga tggaacatgt      600
gagattgatg tttggccttc ccttcagaat tttacctgtg atgtaatttc tcggacggca      660
tttggaagca gctacgcaga aggaacaaaa ctatttcaac ttctaaagaa gcagggattt      720
cttttgatga cagggcgaca cacgaacaat ccattatggg ggcttctagc aacaactacc      780
aagacgaaga tgaaagaaat tgatagagaa atccatgatt cacttgaggg aatcattgaa      840
aaacgagaaa agcactgaa gaatggtgaa accaccaatg acgatttatt aggcattctt       900
ttgcaatcaa atcatgccga aaacaagga caaggaaata gtaagaatat tgggatgacc       960
acccaagatg tgatagatga atgcaaattg ttttaccttg ctgggcaaga gacgacttca      1020
agtttgctgg tttggacaat ggtgttatta ggcaggtatc ctgaatggca agcacgtgca      1080
agggaggaag ttttgcaagt ttttgggaac caaaatccta caacgaagg attaagtcaa       1140
cttaaaattg ttaccatgat tttgtacgag gtactaaggt tattcccacc tttaatttac      1200
ttcaaccgag ctcttcgaaa ggatttgaaa cttggaaacc ttttgctacc tgaaggaaca      1260
caaatttccc taccaatact attgattcac caagatcatg atctatgggg tgatgatgca      1320
aaggagttca aacctgaaag gtttgctgaa ggaattgcga aggcaacaaa aggacaagtt      1380
tcttatttcc cttttggatg gggtcctaga atttgtcttg acaaaacttt tgccttatta      1440
gaagcaaaga tagcagtatc attgttgctg cagaatttct cattcgaact ttctccaaat      1500
tatgtgcatg ttcctaccac ggtgcttact ttgcagccaa aaaatgggc aagcatcatt        1560
ttgcataaac tgtaa                                                        1575
```

<210> SEQ ID NO 18
<211> LENGTH: 524
<212> TYPE: PRT
<213> ORGANISM: Medigago truncatula

<400> SEQUENCE: 18

```
Met Glu Val Phe Met Phe Pro Thr Gly Thr Thr Val Ile Ile Ser Val
1               5                   10                  15

Leu Ser Val Leu Leu Ala Val Ile Pro Trp Tyr Leu Leu Asn Lys Leu
            20                  25                  30

Trp Leu Lys Pro Lys Arg Phe Glu Lys Leu Leu Lys Ala Gln Gly Phe
        35                  40                  45

Gln Gly Glu Pro Tyr Asn Leu Ser Val Leu Lys Asp Lys Ser Lys Gln
    50                  55                  60

Asn Tyr Met Leu Lys Leu Gln Gln Glu Asp Lys Ser Lys Ser Ile Gly
65                  70                  75                  80
```

```
Leu Ser Lys Glu Ala Ala Pro Ser Ile Phe Thr Pro Val His Gln Thr
                85                  90                  95
Val Arg Lys Tyr Gly Asn Asn Ser Phe Leu Trp Glu Gly Thr Thr Pro
            100                 105                 110
Arg Val Ile Ile Thr Asp Pro Asp Gln Ile Lys Asp Val Phe Asn Lys
        115                 120                 125
Ile Asp Asp Phe Pro Lys Pro Lys Leu Arg Ser Ile Ala Lys Tyr Leu
    130                 135                 140
Ser Val Gly Ile Leu Asp His Glu Gly Lys Lys Trp Ala Lys His Arg
145                 150                 155                 160
Lys Ile Ala Asn Pro Ala Phe His Leu Glu Lys Leu Lys Val Met Leu
                165                 170                 175
Pro Ala Phe Ser His Ser Cys Asn Glu Met Ile Ser Lys Trp Lys Glu
            180                 185                 190
Leu Leu Ser Ser Asp Gly Thr Cys Glu Ile Asp Val Trp Pro Ser Leu
        195                 200                 205
Gln Asn Phe Thr Cys Asp Val Ile Ser Arg Thr Ala Phe Gly Ser Ser
    210                 215                 220
Tyr Ala Glu Gly Thr Lys Leu Phe Gln Leu Leu Lys Lys Gln Gly Phe
225                 230                 235                 240
Leu Leu Met Thr Gly Arg His Thr Asn Asn Pro Leu Trp Gly Leu Leu
                245                 250                 255
Ala Thr Thr Thr Lys Thr Lys Met Lys Glu Ile Asp Arg Glu Ile His
            260                 265                 270
Asp Ser Leu Glu Gly Ile Ile Glu Lys Arg Glu Lys Ala Leu Lys Asn
        275                 280                 285
Gly Glu Thr Thr Asn Asp Asp Leu Leu Gly Ile Leu Leu Gln Ser Asn
    290                 295                 300
His Ala Glu Lys Gln Gly Gln Gly Asn Ser Lys Asn Ile Gly Met Thr
305                 310                 315                 320
Thr Gln Asp Val Ile Asp Glu Cys Lys Leu Phe Tyr Leu Ala Gly Gln
                325                 330                 335
Glu Thr Thr Ser Ser Leu Leu Val Trp Thr Met Val Leu Leu Gly Arg
            340                 345                 350
Tyr Pro Glu Trp Gln Ala Arg Ala Arg Glu Glu Val Leu Gln Val Phe
        355                 360                 365
Gly Asn Gln Asn Pro Asn Asn Glu Gly Leu Ser Gln Leu Lys Ile Val
    370                 375                 380
Thr Met Ile Leu Tyr Glu Val Leu Arg Leu Phe Pro Pro Leu Ile Tyr
385                 390                 395                 400
Phe Asn Arg Ala Leu Arg Lys Asp Leu Lys Leu Gly Asn Leu Leu Leu
                405                 410                 415
Pro Glu Gly Thr Gln Ile Ser Leu Pro Ile Leu Leu Ile His Gln Asp
            420                 425                 430
His Asp Leu Trp Gly Asp Asp Ala Lys Glu Phe Lys Pro Glu Arg Phe
        435                 440                 445
Ala Glu Gly Ile Ala Lys Ala Thr Lys Gly Gln Val Ser Tyr Phe Pro
    450                 455                 460
Phe Gly Trp Gly Pro Arg Ile Cys Leu Gly Gln Asn Phe Ala Leu Leu
465                 470                 475                 480
Glu Ala Lys Ile Ala Val Ser Leu Leu Leu Gln Asn Phe Ser Phe Glu
                485                 490                 495
```

```
Leu Ser Pro Asn Tyr Val His Val Pro Thr Thr Val Leu Thr Leu Gln
            500                 505                 510

Pro Lys Asn Gly Ala Ser Ile Ile Leu His Lys Leu
        515                 520

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
caccatggaa gtgtttatgt ttcccacagg                                    30

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
ttacagttta tgcaaaatga tgcttgca                                      28
```

TRITERPENE OXIDASE DERIVED FROM PLANT BELONGING TO GENUS *GLYCYRRHIZA*, GENE ENCODING THE SAME, AND METHOD OF USING THE SAME

TECHNICAL FIELD

The present invention relates to an enzyme that oxidizes oleanane-type triterpene derived from a plant in the family Fabaceae, in particular, a plant belonging to the genus *Glycyrrhiza* or a plant belonging to the genus *Medicago*, a gene encoding the enzyme, a method for manufacturing the enzyme, and a method for using the enzyme or the gene.

BACKGROUND ART

Plants belonging to the genus *Glycyrrhiza* that are perennial herbaceous plants in the family Fabaceae are known as important raw materials for Chinese herbal medicines and widely used around the world. Parts to be used as herbal medicine in the plants are mainly roots and stolons. It has been revealed that a main active ingredient contained in these parts is glycyrrhizin in *G. uralensis*, *G. glabra*, and *G. inflata* belonging to the genus *Glycyrrhiza*. Glycyrrhizin is a sweetener belonging to oleanane-type triterpene saponin (triterpenoid saponin). Various studies such as pharmacognostic study, pharmacological study, and breeding study on glycyrrhizin have been carried out due to its usefulness.

In order to stably and continuously supply high quality glycyrrhizin as medicine by a biological production system, establishment of optimal conditions for production, selection of a high-production strain of glycyrrhizin, breeding of high production plants of glycyrrhizin by introduction of a synthase gene, or the like, are necessary to be carried out by using a biosynthesis-related gene of glycyrrhizin or a gene expression amount of the gene as a marker. In order to do so, identification of a biosynthesis-related gene of glycyrrhizin is essential. As to a synthase gene involved in a biosynthetic pathway of glycyrrhizin, biosynthetic pathways and genes involved in the biosynthetic pathways, after β-amyrin synthase, have hardly been clarified. β-amyrin belongs to oleanane-type triterpene (triterpenoid), and is a precursor from which biosynthesis of glycyrrhizin and soyasaponin diverges in the triterpene saponin biosynthetic pathway (see FIG. 1*a*). To date, as a synthase gene in a pathway from β-amyrin to soyasaponin, a cytochrome P450 oxidase gene CYP93E1, which hydroxylates β-amyrin and sophoradiol at the position 24, has been isolated from soybean (see Patent Literature 1 and Non Patent Literature 1) (see FIG. 1*a*). Furthermore, as a synthase gene in a pathway from β-amyrin to glycyrrhizin, a cytochrome P450 oxidase gene (CYP88D6), which oxidizes carbon at the position 11 of β-amyrin, has been isolated from *Glycyrrhiza* by the present inventors (see Patent Literature 2) (FIG. 1*a* and FIG. 8). However, since the biosynthetic pathway of glycyrrhizin and a synthase gene related thereto have not sufficiently been elucidated, it has not been possible to efficiently obtain glycyrrhizin by a biological production system.

CITATION LIST

Patent Literature

Patent Literature 1: International Publication WO/2005/080572

Patent Literature 2: Japanese Patent Application No. 2007-204769

Non Patent Literature

Non Patent Literature 1: Shibuya et al. Identification of beta-amyrin and sophoradiol 24-hydroxylase by expressed sequence tag mining and functional expression assay. FEBS J. 2006 March; 273 (5):948-59.

DISCLOSURE OF THE INVENTION

Technical Problem

An object of the present invention is to identify an enzyme related to a biosynthetic pathway of glycyrrhizin and having an activity of oxidizing oleanane-type triterpene, and a gene encoding the enzyme, and to provide the enzyme, the gene, and a method for using the same in order to stably and continuously supply glycyrrhizin.

Solution to Problem

The present inventors devoted a full effort to solve the aforementioned problems, and as a result, for the first time, they successfully isolated a novel cytochrome P450 molecular species oxidizing carbon at the position 30 of oleanane-type triterpene in a biosynthetic pathway from β-amyrin to glycyrrhizin, and a gene encoding the same. Specifically, they prepared mRNA from a plant in the family Fabaceae, produced a cDNA library, and carried out an EST analysis. They predicted that a cytochrome P450 gene was involved in the biosynthetic pathway, and retrieved the cDNA library by using the known nucleotide sequence of cytochrome P450 gene to narrow down the candidate genes. They carried out a gene expression analysis with respect to each candidate gene so as to identify a cytochrome P450 molecule gene that has the intended activity and is highly expressed in stolons and roots. Thus, they have completed the present invention. That is to say, the present application provides the following invention.

In the first embodiment, the present invention provides a polypeptide having an activity of oxidizing carbon at the position 30 of oleanane-type triterpene. In one aspect of this embodiment, the oleanane-type triterpene is, for example, β-amyrin, 11-oxo-β-amyrin, or 30-hydroxy-11-oxo-β-amyrin. Furthermore, in another aspect of this embodiment, the polypeptide is derived from plants in the family Fabaceae, preferably, plants in the subfamily Faboideae, for example, plants belonging to the genus *Arachis*, plants belonging to the genus *Cicer*, plants belonging to the genus *Aspalathus*, plants belonging to the genus *Dalbergia*, plants belonging to the genus *Pterocarpus*, plants belonging to the genus *Desmodium*, plants belonging to the genus *Lespedeza*, plants belonging to the genus *Uraria*, plants belonging to the tribe Galegeae, plants belonging to the genus *Astragalus*, plants belonging to the genus *Glycyrrhiza*, plants belonging to the genus *Oxytropis*, plants belonging to the genus *Augyrocytisus*, plants belonging to the genus *Cytisus*, plants belonging to the genus *Genista*, plants belonging to the genus *Spartium*, plants belonging to the genus *Hedysarum*, plants belonging to the genus *Cyamopsis*, plants belonging to the genus *Indigofera*, plants belonging to the genus *Lotus*, plants belonging to the genus *Lupinus*, plants belonging to the genus *Wisteria*, plants belonging to the genus *Cajanus*, plants belonging to the genus *Canavalia*, plants belonging to the genus *Erythrina*, plants belonging to the genus *Glycine*, plants belonging to the genus *Hardenbergia*, plants belonging to the genus *Lablab*, plants belonging to the genus *Mucuna*, plants belonging to the genus *Phaseolus*, plants belonging to the genus *Psophocarpus*, plants belonging to the genus *Pueraria*, plants belonging to the genus *Vigna*, plants belonging to the genus *Robinia*, plants belonging to the genus *Castanospermum*, plants belonging to the genus *Maackia*, plants belonging to the genus *Ormosia*, plants belonging to the genus *Sophora*, plants belonging to the genus *Styphnolobium*, plants belonging to the genus *Medicago*, plants belonging to the genus *Trigonella*, plants belonging to the genus *Trifolium*, plants belonging to the genus *Lathyrus*, plants belonging to the genus *Lens*, plants belonging to the genus *Pisum* and plants belonging to the genus *Vicia*, particularly preferably, plants belonging to the genus *Glycyrrhiza* or plants belonging to the genus *Medicago*, and further more preferably, *G. uralensis, G. glabra* or *M. truncatula*. In still another aspect of this embodiment, the polypeptide is protein belonging to cytochrome P450. In yet another aspect of this embodiment, the above-mentioned polypeptide has any of (a) an amino acid sequence shown in SEQ ID NO: 4, 14 or 18, (b) an amino acid sequence comprising deletion, substitution, or addition of one or several amino acids in the amino acid sequence shown in SEQ ID NO: 4, 14 or 18, or (c) an amino acid sequence having 80% or more identity with the amino acid sequence shown in SEQ ID NO: 4, 14 or 18.

In the second embodiment, the present invention provides a polynucleotide encoding the polypeptide described in the first embodiment. In one aspect of this embodiment, the oleanane-type triterpene is β-amyrin, 11-oxo-β-amyrin, or 30-hydroxy-11-oxo-β-amyrin. Furthermore, in another aspect of this embodiment, the polynucleotide is derived from plants in the family Fabaceae, preferably, plants in the subfamily Faboideae, for example, plants belonging to the genus *Arachis*, plants belonging to the genus *Cicer*, plants belonging to the genus *Aspalathus*, plants belonging to the genus *Dalbergia*, plants belonging to the genus *Pterocarpus*, plants belonging to the genus *Desmodium*, plants belonging to the genus *Lespedeza*, plants belonging to the genus *Uraria*, plants belonging to the tribe Galegeae, plants belonging to the genus *Astragalus*, plants belonging to the genus *Glycyrrhiza*, plants belonging to the genus *Oxytropis*, plants belonging to the genus *Augyrocytisus*, plants belonging to the genus *Cytisus*, plants belonging to the genus *Genista*, plants belonging to the genus *Spartium*, plants belonging to the genus *Hedysarum*, plants belonging to the genus *Cyamopsis*, plants belonging to the genus *Indigofera*, plants belonging to the genus *Lotus*, plants belonging to the genus *Lupinus*, plants belonging to the genus *Wisteria*, plants belonging to the genus *Cajanus*, plants belonging to the genus *Canavalia*, plants belonging to the genus *Erythrina*, plants belonging to the genus *Glycine*, plants belonging to the genus *Hardenbergia*, plants belonging to the genus *Lablab*, plants belonging to the genus *Mucuna*, plants belonging to the genus *Phaseolus*, plants belonging to the genus *Psophocarpus*, plants belonging to the genus *Pueraria*, plants belonging to the genus *Vigna*, plants belonging to the genus *Robinia*, plants belonging to the genus *Castanospermum*, plants belonging to the genus *Maackia*, plants belonging to the genus *Ormosia*, plants belonging to the genus *Sophora*, plants belonging to the genus *Styphnolobium*, plants belonging to the genus *Medicago*, plants belonging to the genus *Trigonella*, plants belonging to the genus *Trifolium*, plants belonging to the genus *Lathyrus*, plants belonging to the genus *Lens*, plants belonging to the genus *Pisum* and plants belonging to the genus *Vicia*, particularly preferably, plants belonging to the genus *Glycyrrhiza* or plants belonging to the genus *Medi-cago*, and further more preferably, *G. uralensis, G. glabra* or *M. truncatula*. In still another aspect of this embodiment, the polynucleotide encodes protein belonging to cytochrome P450. In yet another aspect of this embodiment, the polynucleotide has any of (d) a nucleotide sequence shown in SEQ ID NO: 3, 13 or 17, (e) a nucleotide sequence comprising deletion, substitution, or addition of one or several nucleotides in the nucleotide sequence shown in SEQ ID NO: 3, 13 or 17, (f) a nucleotide sequence having 80% or more identity with the nucleotide sequence shown in SEQ ID NO: 3, 13 or 17, or (g) a nucleotide sequence hybridizing to a nucleotide sequence complementary to the nucleotide sequence shown in SEQ ID NO: 3, 13 or 17 under stringent conditions.

In the third embodiment, the present invention provides a recombinant vector comprising the polynucleotide described in the second embodiment.

In the fourth embodiment, the present invention provides a transformant comprising the polynucleotide described in the second embodiment and/or the recombinant vector described in the third embodiment. In one aspect of this embodiment, the transformant is a plant in the family Fabaceae, preferably a plant in the subfamily Faboideae, for example, a plant belonging to the genus *Arachis*, a plant belonging to the genus *Cicer*, a plant belonging to the genus *Aspalathus*, a plant belonging to the genus *Dalbergia*, a plant belonging to the genus *Pterocarpus*, a plant belonging to the genus *Desmodium*, a plant belonging to the genus *Lespedeza*, a plant belonging to the genus *Uraria*, plants belonging to the tribe Galegeae, a plant belonging to the genus *Astragalus*, plants belonging to the genus *Glycyrrhiza*, a plant belonging to the genus *Oxytropis*, a plant belonging to the genus *Augyrocytisus*, a plant belonging to the genus *Cytisus*, a plant belonging to the genus *Genista*, a plant belonging to the genus *Spartium*, a plant belonging to the genus *Hedysarum*, a plant belonging to the genus *Cyamopsis*, a plant belonging to the genus *Indigofera*, a plant belonging to the genus *Lotus*, a plant belonging to the genus *Lupinus*, a plant belonging to the genus *Wisteria*, a plant belonging to the genus *Cajanus*, a plant belonging to the genus *Canavalia*, a plant belonging to the genus *Erythrina*, a plant belonging to the genus *Glycine*, a plant belonging to the genus *Hardenbergia*, a plant belonging to the genus *Lablab*, a plant belonging to the genus *Mucuna*, a plant belonging to the genus *Phaseolus*, a plant belonging to the genus *Psophocarpus*, a plant belonging to the genus *Pueraria*, a plant belonging to the genus *Vigna*, a plant belonging to the genus *Robinia*, a plant belonging to the genus *Castanospermum*, a plant belonging to the genus *Maackia*, a plant belonging to the genus *Ormosia*, a plant belonging to the genus *Sophora*, a plant belonging to the genus *Styphnolobium*, a plant belonging to the genus *Medicago*, a plant belonging to the genus *Trigonella*, a plant belonging to the genus *Trifolium*, a plant belonging to the genus *Lathyrus*, a plant belonging to the genus *Lens*, a plant belonging to the genus *Pisum* and a plant belonging to the genus *Vicia*, particularly preferably, a plant belonging to the genus *Glycyrrhiza* or a plant belonging to the genus *Medicago*, and further more preferably, *G. uralensis, G. glabra* or *M. truncatula*. In another aspect of this embodiment, in the transformant, expression of the polynucleotide described in the second embodiment is enhanced or suppressed.

In the fifth embodiment, the present invention provides a method for manufacturing a polypeptide, which comprises culturing or growing the transformant described in the fourth embodiment, and extracting a polypeptide described in the first embodiment from the cultured product or the grown product.

In the sixth embodiment, the present invention provides a method for manufacturing glycyrrhetinic acid and 20-epi-glycyrrhetinic acid, the method comprising allowing a polypeptide described in the first embodiment and a polypeptide having an activity oxidizing carbon at the position 11 of oleanane-type triterpene to act on oleanane-type triterpene.

In the seventh embodiment, the present invention provides a method for selecting a plant by determining the presence or absence or expression of the polypeptide described in the first embodiment in a plant. The method comprises detecting or quantifying the polynucleotide by carrying out a nucleic acid amplification method or nucleic acid hybridization for a sample containing a nucleic acid prepared from the plant by using the polynucleotide or a fragment thereof.

Note here that glycyrrhizin, a biosynthetic pathway from β-amyrin to glycyrrhizin, and an intermediate product of the pathway in this specification include 20-epi-glycyrrhizin that is an isomer at position 20 of glycyrrhizin, a biosynthetic pathway from β-amyrin to 20-epi-glycyrrhizin, and an intermediate product of the pathway unless otherwise noted.

Advantageous Effects of Invention

The present invention can provide a polypeptide that is involved in a biosynthetic pathway of glycyrrhizin and that oxidizes carbon at the position 30 of oleanane-type triterpene, a polynucleotide encoding the polypeptide, or a method of using the same.

DESCRIPTION OF EMBODIMENTS

Figure 1:
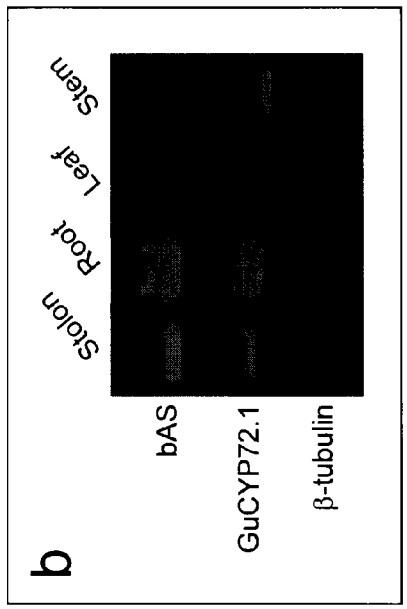
FIG. 1 shows biosynthetic pathways of glycyrrhizin and soyasaponin I, and results of gene expression analysis by a RT-PCR method.
Figure 1:
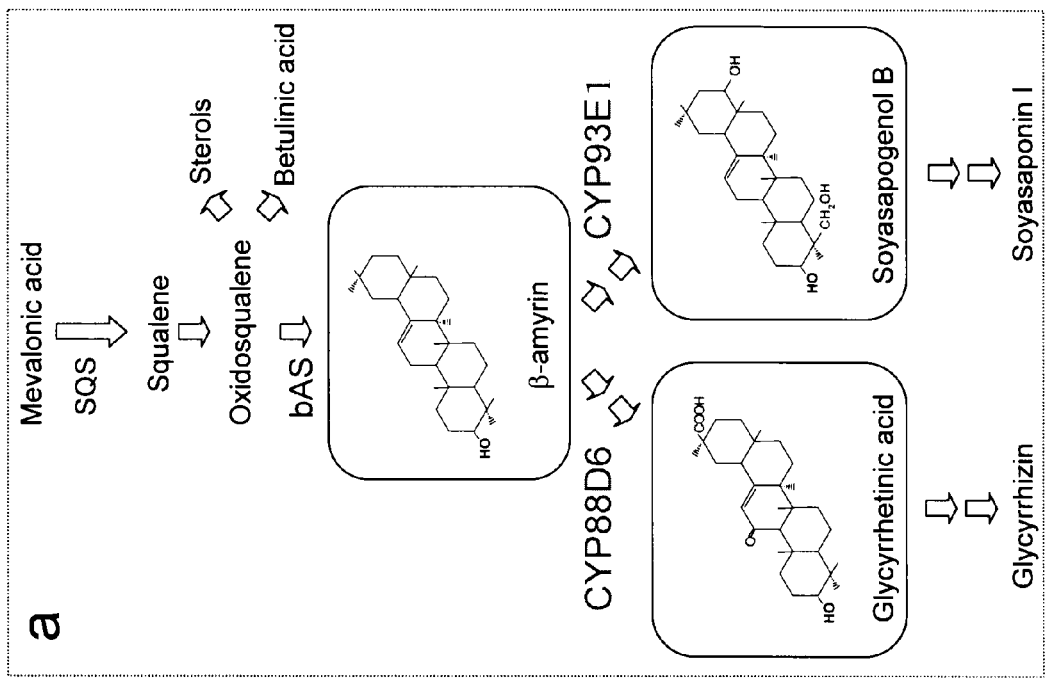

Hereinafter, the present invention is described in detail.

Embodiment 1

The invention of Embodiment 1 relates to a polypeptide having an activity of oxidizing carbon at the position 30 of oleanane-type triterpene. The oleanane-type triterpene is C30 isoprenoid having five membered oleanane skeleton and consisting of six isoprene units. Examples of the oleanane-type triterpene include oleanolic acid, hederagenin, β-amyrin, camelliagenin, soyasapogenol, saikogenin, 11-oxo-β-amyrin, and 30-hydroxy-11-oxo-β-amyrin. However, the oleanane-type triterpene is not limited to these examples. For the oleanane-type triterpene of the present invention, β-amyrin, 11-oxo-β-amyrin, and 30-hydroxy-11-oxo-β-amyrin are particularly preferable.

The polypeptide of the present invention is not particularly limited as long as it is a polypeptide having an activity of oxidizing carbon at the position 30 of oleanane-type triterpene. In one aspect, the polypeptide of the present invention is a polypeptide belonging to cytochrome P450. Cytochrome P450 (CYP) is a group of reduced protoheme-containing protein enzymes that are known as drug metabolizing enzymes. Each enzyme catalyzes a monooxygenation reaction in which a single oxygen atom is allowed to bind to substrate by an electron donor such as NAD(P)H and oxygen, and at the same time water is generated. The molecular species and organism species of cytochrome P450 of the present invention are not particularly limited as long as they have the above-mentioned activity. Furthermore, in another aspect, the polypeptide of the present invention is derived from plants in the family Fabaceae, preferably plants in the subfamily Faboideae, for example, plants belonging to the genus *Arachis*, plants belonging to the genus *Cicer*, plants belonging to the genus *Aspalathus*, plants belonging to the genus *Dalbergia*, plants belonging to the genus *Pterocarpus*, plants belonging to the genus *Desmodium*, plants belonging to the genus *Lespedeza*, plants belonging to the genus *Uraria*, plants belonging to the tribe Galegeae, plants belonging to the genus *Astragalus*, plants belonging to the genus *Glycyrrhiza*, plants belonging to the genus *Oxytropis*, plants belonging to the genus *Augyrocytisus*, plants belonging to the genus *Cytisus*, plants belonging to the genus *Genista*, plants belonging to the genus *Spartium*, plants belonging to the genus *Hedysarum*, plants belonging to the genus *Cyamopsis*, plants belonging to the genus *Indigofera*, plants belonging to the genus *Lotus*, plants belonging to the genus *Lupinus*, plants belonging to the genus *Wisteria*, plants belonging to the genus *Cajanus*, plants belonging to the genus *Canavalia*, plants belonging to the genus *Erythrina*, plants belonging to the genus *Glycine*, plants belonging to the genus *Hardenbergia*, plants belonging to the genus *Lablab*, plants belonging to the genus *Mucuna*, plants belonging to the genus *Phaseolus*, plants belonging to the genus *Psophocarpus*, plants belonging to the genus *Pueraria*, plants belonging to the genus *Vigna*, plants belonging to the genus *Robinia*, plants belonging to the genus *Castanospermum*, plants belonging to the genus *Maackia*, plants belonging to the genus *Ormosia*, plants belonging to the genus *Sophora*, plants belonging to the genus *Styphnolobium*, plants belonging to the genus *Medicago*, plants belonging to the genus *Trigonella*, plants belonging to the genus *Trifolium*, plants belonging to the genus *Lathyrus*, plants belonging to the genus *Lens*, plants belonging to the genus *Pisum* and plants belonging to the genus *Vicia*, particularly preferably, plants belonging to the genus *Glycyrrhiza* or plants belonging to the genus *Medicago*, and further more preferably, *G. uralensis, G. glabra* or *M. truncatula*. Furthermore, in still another aspect, the polypeptide of the present invention is preferably a polypeptide having (a) an amino acid sequence shown in SEQ ID NO: 4, 14 or 18. Herein, polypeptide shown in SEQ ID NO: 4 corresponds to one molecular species (GuCYP72.1) of cytochrome P450 in *G. uralensis*. Furthermore, polypeptide shown in SEQ ID NO: 14 corresponds to one molecular species (GgCYP72.1) of cytochrome P450 in *G. glabra*. Furthermore, polypeptide shown in SEQ ID NO: 18 corresponds to one molecular species (MtCYP72.1) of cytochrome P450 in *M. truncatula*. In addition, the polypeptide of the present invention may be a polypeptide having (b) an amino acid sequence comprising deletion, substitution, or addition of one or several amino acids in the amino acid sequence shown in SEQ ID NO: 4, 14 or 18, and having an activity of oxidizing carbon at the position 30 of oleanane-type triterpene. Alternatively, the polypeptide of the present invention may be a polypeptide having (c) an amino acid sequence having 80% or more identity with the amino acid sequence shown in SEQ ID NO: 4, 14 or 18, and having an activity of oxidizing carbon at the position 30 of oleanane-type triterpene.

The phrase "an amino acid sequence comprising deletion, substitution, or addition of one or several amino acids in the amino acid sequence shown in SEQ ID NO: 4, 14 or 18" means that, for example, one to ten amino acid(s), preferably one to five amino acid(s), and more preferably one to three amino acid(s) are deleted from the amino acid sequence shown in SEQ ID NO: 4, 14 or 18; one to ten amino acid(s), preferably one to five amino acid(s), and more preferably one to three amino acid(s) are added to the amino acid sequence shown in SEQ ID NO: 4, 14 or 18; or one to ten amino acid(s), preferably one to five amino acid(s) and more preferably one to three amino acid(s) in the amino acid sequence shown in SEQ ID NO: 4, 14 or 18 are substituted by other amino acid(s). One example is a single amino acid substituted mutant of cytochrome P450 shown in SEQ ID NO: 4, 14 or 18, having an activity of oxidizing carbon at the position 30 of oleanane-type triterpene.

The "identity" in this embodiment is 80% or more identity, preferably 85% or more identity, more preferably 90% identity, further preferably 95% identity, and further more preferably 97% or more identity with respect to the amino acid sequence shown in SEQ ID NO: 4, 14 or 18. Furthermore, an example of the "polypeptide having an amino acid sequence having 80% or more identity with the amino acid sequence shown in SEQ ID NO: 4, 14 or 18, and having an activity of oxidizing carbon at the position 30 of oleanane-type triterpene" includes a polypeptide encoded by an orthologous gene of other organism species of a gene for a protein belonging to cytochrome P450 of *G. uralensis* (SEQ ID NO: 3), or a polypeptide encoded by a paralogous gene shown in SEQ ID NO: 3 and having the same function as that of the polypeptide shown in SEQ ID NO: 4.

In addition, the polypeptide of the present invention may be fragments of the polypeptide shown in the above-mentioned (a) to (c) having an activity of oxidizing carbon at the position 30 of oleanane-type triterpene. This is because the main object of the present invention is to oxidize carbon at the position 30 of oleanane-type triterpene, and therefore, full-length polypeptide, for example, polypeptide shown in SEQ ID NO: 4, 14 or 18, is not necessarily needed as long as the polypeptide has the above-mentioned activity. Herein, the "fragments of the polypeptide" refers to a region of at least 10, 15, 20, 25, 30, 50, 100, or 150 continuous amino acids in the polypeptide shown in the above-mentioned (a) to (c).

The origin organism species of the polypeptide of the present invention is not particularly limited, but it is preferably, plants in the family Fabaceae, and more preferably plants in the subfamily Faboideae, for example, plants belonging to the genus *Arachis*, plants belonging to the genus *Cicer*, plants belonging to the genus *Aspalathus*, plants belonging to the genus *Dalbergia*, plants belonging to the genus *Pterocarpus*, plants belonging to the genus *Desmodium*, plants belonging to the genus *Lespedeza*, plants belonging to the genus *Uraria*, plants belonging to the tribe Galegeae, plants belonging to the genus *Astragalus*, plants belonging to the genus *Glycyrrhiza*, plants belonging to the genus *Oxytropis*, plants belonging to the genus *Augyrocytisus*, plants belonging to the genus *Cytisus*, plants belonging to the genus *Genista*, plants belonging to the genus *Spartium*, plants belonging to the genus *Hedysarum*, plants belonging to the genus *Cyamopsis*, plants belonging to the genus *Indigofera*, plants belonging to the genus *Lotus*, plants belonging to the genus *Lupinus*, plants belonging to the genus *Wisteria*, plants belonging to the genus *Cajanus*, plants belonging to the genus *Canavalia*, plants belonging to the genus *Erythrina*, plants belonging to the genus *Glycine*, plants belonging to the genus *Hardenbergia*, plants belonging to the genus *Lablab*, plants belonging to the genus *Mucuna*, plants belonging to the genus *Phaseolus*, plants belonging to the genus *Psophocarpus*, plants belonging to the genus *Pueraria*, plants belonging to the genus *Vigna*, plants belonging to the genus *Robinia*, plants belonging to the genus *Castanospermum*, plants belonging to the genus *Maackia*, plants belonging to the genus *Ormosia*, plants belonging to the genus *Sophora*, plants belonging to the genus *Styphnolobium*, plants belonging to the genus *Medicago*, plants belonging to the genus *Trigonella*, plants belonging to the genus *Trifolium*, plants belonging to the genus *Lathyrus*, plants belonging to the genus *Lens*, plants belonging to the genus *Pisum* and plants belonging to the genus *Vicia*, particularly preferably, plants belonging to the genus *Glycyrrhiza* or plants belonging to the genus *Medicago*. The plants belonging to the genus *Glycyrrhiza* are the plants classified into the genus *Glycyrrhiza* in the family Fabaceae, and specific examples thereof include *G. uralensis, G. glabra, G. inflata, G. aspera, G. eurycarpa, G. pallidiflora, G. yunnanensis, G. lepidota, G. echinata, G. acanthocarpa*, and the like. Among them, *G. uralensis* and *G. glabra* are particularly preferable as an origin organism species of polypeptide of the present invention. Furthermore, the plants belonging to the genus *Medicago* are plants classified into the genus *Medicago* in the family Fabaceae, and specific examples thereof include *M. truncatula, M. sativa, M. polymorpha, M. arabica, M. hispida, M. minima, M. scutellata, M. murex, M. lupilina*, and the like. Among them, *M. truncatula* is particularly preferable as origin organism species of the polypeptide of the present invention.

While the polypeptide of the present invention can be obtained from, for example, stolons or roots of plants belonging to the genus *Glycyrrhiza* or plants belonging to the genus *Medicago* by using known methods, a polypeptide having an amino acid sequence shown in SEQ ID NO: 4, 14 or 18 may be synthesized by known chemical synthesis methods, and may be obtained by biosynthesis by obtaining a gene encoding the polypeptide mentioned below, and by using known gene recombination technology, and a protein expression system using *Escherichia coli*, yeast, insect cells, and mammalian cells.

The amino acid sequence comprising deletion, substitution, or addition of one or several amino acids in the amino acid sequence shown in SEQ ID NO: 4, 14 or 18, or an amino acid sequence having 80% or more identity with the amino acid sequence shown in SEQ ID NO: 4, 14 or 18 can be obtained by, for example, modifying polynucleotide described in Embodiment 2 by methods known to the technical field. For example, a mutation can be introduced into a gene by known methods such as Kunkel method or a Gapped duplex method or methods corresponding to such methods. Mutation may be introduced by using commercially available mutation introducing kits using a site-directed mutagenesis method (for example, Mutant-K (TaKaRa) or Mutant-G (TaKaRa)), or LA PCR in vitro Mutagenesis series kit (TaKaRa), and the like. Furthermore, a method of bringing a gene into contact with a mutagenic agent (for example, alkylating agent such as ethyl methanesulfonate and N-methyl-N'-nitro-N-nitrosoguanidine), a method of irradiating a gene with ultraviolet ray, can be used.

Furthermore, the polypeptide of the present invention is allowed to act on oleanane-type triterpene so as to oxidize carbon at the position 30 of the triterpene. For example, by allowing the polypeptide of Embodiment 1 to act on β-amyrin, 11-oxo-β-amyrin, or 30-hydroxy-11-oxo-β-amyrin, which are substrates, each carbon at position 30 can be oxidized.

The polypeptide of this embodiment can oxidize carbon at the position 30 of oleanane-type triterpene. Furthermore, it is possible to provide a method for oxidizing carbon at the position 30 of oleanane-type triterpene by using the polypeptide of the present invention. Therefore, the use of the polypeptide and oxidization method can be applied for further elucidation of a biosynthetic pathway of glycyrrhizin or synthesis of glycyrrhizin.

Embodiment 2

The invention of Embodiment 2 relates to a polynucleotide encoding the polypeptide described in Embodiment 1. In one aspect of this embodiment, the polynucleotide of the present invention is a polynucleotide encoding the polypeptide belonging to cytochrome P450 described in Embodiment 1.

The polynucleotide of the present invention is not particularly limited as long as it is a polynucleotide encoding the polypeptide described in Embodiment 1. Preferably, it is a polynucleotide having (d) a nucleotide sequence shown in SEQ ID NO: 3, 13 or 17. The polynucleotide having a nucleotide sequence shown in SEQ ID NO: 3 encodes one molecular species (GuCYP72.1) of cytochrome P450 in *G. uralensis*. Furthermore, the polynucleotide having a nucleotide sequence shown in SEQ ID NO: 13 encodes one molecular species (GgCYP72.1) of cytochrome P450 in *G. glabra*. Furthermore, the polynucleotide having a nucleotide sequence shown in SEQ ID NO: 17 encodes one molecular species (MtCYP72.1) of cytochrome P450 in *M. truncatula*. In addition, the polynucleotide of the present invention may be a polynucleotide having (e) a nucleotide sequence comprising deletion, substitution, or addition of one or several nucleotides in the nucleotide sequence shown in SEQ ID NO: 3, 13 or 17, and having a nucleotide sequence encoding the polypeptide described in Embodiment 1. Alternatively, the polynucleotide of the present invention may be a polynucleotide having (f) a nucleotide sequence having 80% or more identity with the nucleotide sequence shown in SEQ ID NO: 3, 13 or 17, and having a nucleotide sequence encoding the polypeptide described in Embodiment 1. Furthermore, the polynucleotide of the present invention may be a polynucleotide having (g) a nucleotide sequence hybridizing to a nucleotide sequence complementary to the nucleotide sequence shown in SEQ ID NO: 3, 13 or 17 under stringent conditions, and having a nucleotide sequence encoding the polypeptide described in Embodiment 1.

In the present invention, the "nucleotide sequence comprising deletion, substitution, or addition of one or several nucleotides in the nucleotide sequence shown in SEQ ID NO: 3, 13 or 17" means, for example, a nucleotide sequence in which 1 to 15 nucleotide(s), preferably 1 to 9 nucleotide(s), and more preferably 3 to 6 nucleotides are deleted in the nucleotide sequence shown in SEQ ID NO: 3; a nucleotide sequence in which 1 to 15 nucleotide(s), preferably 1 to 9 nucleotide(s), and more preferably 3 to 6 nucleotides are added in the nucleotide sequence shown in SEQ ID NO: 3 or 13; or a nucleotide sequence in which 1 to 10 nucleotide(s), preferably 1 to 5 nucleotide(s), and more preferably 1 to 3 nucleotide(s) are substituted with other nucleotides in the nucleotide sequence shown in SEQ ID NO: 3.

The "identity" of the nucleotide sequence in this embodiment is 80% or more identity, preferably 85% or more identity, more preferably 90% identity, further preferably 95% or more identity, and further more preferably 97% or more identity.

In the present invention, the "stringent conditions" refer to such conditions under which a specific hybrid is formed, that is to say, a non-specific hybrid is not substantially formed. An example of such conditions includes conditions under which a complementary strand of a highly identical nucleic acid, namely, a nucleic acid composed of a nucleotide sequence having 80% or more, preferably 85% or more, more preferably 90% or more, and further more preferably 95% or more identity with respect to the nucleotide sequence shown in SEQ ID NO: 3, 13, or 17 hybridizes, while a complementary strand of a nucleic acid with less identity does not hybridize. More specifically, such conditions refer to conditions under which the sodium salt concentration is 15 to 750 mM, preferably 15 to 500 mM, and more preferably 15 to 300 mM or 15 to 200 mM, the temperature is 25 to 70° C., preferably 50 to 70° C., and more preferably 55 to 68° C., and/or the formamide concentration is 0 to 50%, preferably 20 to 50%, and more preferably 35 to 45%. Furthermore, conditions for washing a filter after hybridization under stringent conditions normally includes the sodium salt concentration of 15 to 750 mM, preferably 15 to 500 mM, and more preferably 15 to 300 mM or 15 to 200 mM, and/or the temperature of 50 to 70° C., preferably 55 to 70° C., and more preferably 60 to 65° C.

Besides, the polynucleotide of the present invention may be fragments of the polynucleotide described in the above-mentioned (d) to (g) encoding the polypeptide having an activity of oxidizing carbon at the position 30 of oleanane-type triterpene. Herein, the "fragment of the polynucleotide" refers to a region of at least 10, 15, 20, 25, 30, 50, 100, or 150 continuous nucleotides in the nucleotide sequence of polynucleotide described in the above-mentioned (d) to (g).

Furthermore, the polynucleotide of the present invention may include a nucleotide sequence before splicing, that is to say, a nucleotide sequence corresponding to a mRNA precursor containing intron. This is because a nucleotide sequence on the genome corresponding to the nucleotide sequence of such a mRNA precursor becomes substantially the same sequence as that of the polynucleotide of the present invention by the splicing reaction after gene expression, that is, after transcription, and a polypeptide encoded by the polynucleotide is capable of having substantially the same function as that of the polypeptide described in Embodiment 1. For example, such polynucleotide includes a polynucleotide having a nucleotide sequence existing on a *G. uralensis* genome and having the nucleotide sequence shown in SEQ ID NO: 3 as a nucleotide sequence of the mature mRNA after splicing.

The polynucleotide or the fragment thereof of the present invention can be isolated from a plant in the family Fabaceae by using known methods. For example, it can be obtained by carrying out PCR amplification using a nucleic acid derived from a DNA library or a genomic DNA library or the like of *G. uralensis, G. glabra*, or *M. truncatula* as a template and using a primer having an appropriate nucleotide sequence length, which is designed based on the nucleotide sequence shown in SEQ ID NO: 3, 13 or 17. Furthermore, the polynucleotide of the present invention can be obtained by carrying out hybridization using a nucleic acid derived from the above-mentioned library or the like as a template, and employing a nucleic acid fragment with an appropriate nucleotide sequence length, which is a part of the polynucleotide, as a probe. Alternatively, the polynucleotide of the present invention may be synthesized by a known nucleic acid sequence synthesis method such as a chemical synthesis method.

Furthermore, the nucleotide sequence comprising deletion, substitution, or addition of one or several nucleotides in the nucleotide sequence shown in SEQ ID NO: 3, 13 or 17, or a nucleotide sequence having 80% or more identity with respect to the nucleotide sequence shown in SEQ ID NO: 3, 13, or 17 can be produced by, for example, introducing a mutation by the method described in Embodiment 1.

The polynucleotide of this embodiment can be introduced into various organism species or cells of, for example, plants in the family Fabaceae directly or in a state in which it is introduced into a recombinant vector of Embodiment 3, and allowed to be highly expressed. Thereby, it is possible to enhance the production amount of glycyrrhizin.

Embodiment 3

The invention of Embodiment 3 relates to a recombinant vector comprising the polynucleotide described in the above-mentioned Embodiment 2.

The recombinant vector of the present invention can be constructed by introducing the polynucleotide described in Embodiment 2 into an appropriate vector. The kind of a vector is not particularly limited. A vector can be appropriately selected depending upon purposes (for example, for cloning, or for gene expression) or hosts to which a vector is introduced (for example, *Escherichia coli*, yeast, an insect cell, an animal cell, a plant cell, or a plant body, in particular, a plant in the family Fabaceae). Although it is not limited, specific examples of vectors to be used may include, for example, a plasmid vector such as pBI-based, pPZP-based, pSMA-based, pUC-based, pBR-based, pBluescript-based (Stratagene), and pTriEXTM-based (TaKaRa) vectors, a virus vector such as a cauliflower mosaic virus (CaMV), a bean golden mosaic virus (BGMV), and a tobacco mosaic virus (TMV), or a binary vector such as a pBI-based vector.

As a method for inserting the polynucleotide of interest into the vector, known methods in this technical field can be used. Usually, a method, in which the purified polynucleotide described in Embodiment 2 or the fragment thereof is cleaved by an appropriate restriction enzyme and inserted into and connected to a corresponding restriction site or the multicloning site in the above-mentioned appropriate vector, and the like is employed. As to the specific method, see, for example, Sambrook, J. et. al., (1989) Molecular Cloning: a Laboratory Manual Second Ed., Cold Spring Harbor Laboratory Press, Cold Spring Harbor, N.Y.

To the recombinant vector of the present invention, in addition to the polynucleotide of interest, the regulatory regions, for example, a promoter, an enhancer, a terminator, or the like, or a selection marker gene and/or other genes such as a β-amyrin synthase, can be connected.

The kinds of the promoter, enhancer, terminator or selection marker are not particularly limited. They may be appropriately selected depending upon purposes (for example, cloning, gene expression, or screening), or depending upon hosts to which they are introduced (for example, a bacterium, yeast, an insect cell, an animal cell, a plant cell, or a plant body).

Examples of a promoter operable in a plant cell include a cauliflower mosaic virus (CaMV) 35S promoter, a promoter of a nopaline synthase gene (Pnos), a ubiquitin promoter derived from corn, an actin promoter derived from rice, a PR protein promoter derived from tobacco, and the like. Also, examples of a promoter operable in a bacterial cell include a promoter of a *Bacillus stearothermophilus* maltogenic amylase gene, a *Bacillus licheniformis* α-amylase gene, a *Bacillus amyloliquefaciens* BAN amylase gene, a *Bacillus subtilis* alkaline protease gene, or a *Bacillus pumilus* xylosidase gene, or a PR or PL promoter of a phage lambda, and a lac, trp, or tac promoter of an *Escherichia coli*, and the like. Examples of a promoter operable in a yeast host cell include a promoter derived from a gene involved in a yeast glycolysis system, an alcohol dehydrogenase gene promoter, a TPI 1 promoter, an ADH2-4c promoter, and the like. Examples of a promoter operable in a fungus include an ADH3 promoter, a tpiA promoter, and the like. Examples of a promoter operable in an animal cell include a SV40 early promoter, a SV 40 late promoter, a CMV promoter, and the like, and examples of a promoter operable in an insect cell include a polyhedrin promoter, a P10 promoter, an autographa californica polyhedrosis basic protein promoter, a baculovirus immediate early gene 1 promoter, a baculovirus 39K delayed-early gene promoter, and the like.

Examples of an enhancer include an enhancer region in a CaMV 35S promoter containing an upstream sequence, a SV40 enhancer, a CMV enhancer, and the like.

Examples of a terminator include a terminator of a nopaline synthase (NOS) gene, a terminator of an octopine-synthase (OCS) gene, a CaMV 35S terminator, a 3' terminator of an *Escherichia coli* lipopolyprotein 1pp, trp operon terminator, amyB terminator, a terminator of an ADH1 gene, and the like.

Examples of a selection marker gene include a drug resistance gene (for example, a tetracycline resistance gene, an ampicillin resistance gene, a kanamycin resistance gene, a hygromycin resistance gene, a spectinomycin resistance gene, a chloramphenicol resistance gene, or a neomycin resistance gene), a fluorescent or luminescent reporter gene (for example, a luciferase, a β-galactosidase, a β-glucuronidase (GUS), or a green fluorescent protein (GFP)), and a gene for an enzyme such as a neomycin phosphotransferase II (NPT II) and a dihydrofolate reductase.

The recombinant vector of this embodiment facilitates operation and/or regulation of the polynucleotide described in Embodiment 2.

Embodiment 4

Embodiment 4 relates to a transformant having a polynucleotide described in Embodiment 2 or recombinant vector described in Embodiment 3.

The transformant of the present invention can be produced by introducing the above-described polynucleotide or recombinant vector into an appropriate host. At this time, the transformant of the present invention may include one or more other polynucleotides or other recombinant vectors in addition to the polynucleotide described in Embodiment 2 or the recombinant vector described in Embodiment 3. The other polynucleotide herein refers to polynucleotide other than the polynucleotide described in Embodiment 2. One example is a β-amyrin synthase gene. Furthermore, the other recombinant vector refers to a recombinant vector other than the recombinant vector described in Embodiment 3. A host is not limited as long as an introduced polynucleotide can be expressed. Examples include bacteria (for example, *Escherichia coli*, or *Bacillus subtilis*), yeast (for example, *Saccharomyces cerevisiae, Schizosaccharomyces pombe*, or *Pichia pastoris*), a fungus (*Aspergillus, Neurospora, Fuzarium*, or *Trichoderma*), a monocotyledonous plant (for example, Gramineae), or a dicotyledonous plant (for example, Fabaceae, or Brassicaceae), or a plant cell, an animal cell, or an insect cell (for example, sf9 or sf21).

Examples of methods for introducing a polynucleotide or a recombinant vector include a known method in this technical field, for example, an Agrobacterium method, a PEG-calcium phosphate method, an electroporation method, a liposome method, a particle gun method, and a microinjection method. An introduced polynucleotide may be incorporated into a host genome DNA or present in a state of the introduced polynucleotide (for example, in the form of being comprised in an exogenous vector). Furthermore, the introduced polynucleotide may be continued to be maintained in a host cell as in the case in which it is introduced in a host genome DNA for instance, or may be held temporarily.

After introduction of the polynucleotide described in Embodiment 2 or the recombinant vector described in Embodiment 3 into a host according to the above-described methods, whether or not the polynucleotide of interest has been introduced in the host can be confirmed by a PCR method, a Southern hybridization method, a Northern hybridization method, in situ hybridization, and the like.

When the transformant is a plant, it is preferably a plant in the family Fabaceae, more preferably a plant belonging to the subfamily Faboideae, for example, a plant belonging to the genus *Arachis*, a plant belonging to the genus *Cicer*, a plant belonging to the genus *Aspalathus*, a plant belonging to the genus *Dalbergia*, a plant belonging to the genus *Pterocarpus*, a plant belonging to the genus *Desmodium*, a plant belonging to the genus *Lespedeza*, a plant belonging to the genus *Uraria*, plants belonging to the tribe Galegeae, a plant belonging to the genus *Astragalus*, plants belonging to the genus *Glycyrrhiza*, a plant belonging to the genus *Oxytropis*, a plant belonging to the genus *Augyrocytisus*, a plant belonging to the genus *Cytisus*, a plant belonging to the genus *Genista*, a plant belonging to the genus *Spartium*, a plant belonging to the genus *Hedysarum*, a plant belonging to the genus *Cyamopsis*, a plant belonging to the genus *Indigofera*, a plant belonging to the genus *Lotus*, a plant belonging to the genus *Lupinus*, a plant belonging to the genus *Wisteria*, a plant belonging to the genus *Cajanus*, a plant belonging to the genus *Canavalia*, a plant belonging to the genus *Erythrina*, a plant belonging to the genus *Glycine*, a plant belonging to the genus *Hardenbergia*, a plant belonging to the genus *Lablab*, a plant belonging to the genus *Mucuna*, a plant belonging to the genus *Phaseolus*, a plant belonging to the genus *Psophocarpus*, a plant belonging to the genus *Pueraria*, a plant belonging to the genus *Vigna*, a plant belonging to the genus *Robinia*, a plant belonging to the genus *Castanospermum*, a plant belonging to the genus *Maackia*, a plant belonging to the genus *Ormosia*, a plant belonging to the genus *Sophora*, a plant belonging to the genus *Styphnolobium*, a plant belonging to the genus *Medicago*, a plant belonging to the genus *Trigonella*, a plant belonging to the genus *Trifolium*, a plant belonging to the genus *Lathyrus*, a plant belonging to the genus *Lens*, a plant belonging to the genus *Pisum* and a plant belonging to the genus *Vicia*, particularly preferably, a plant belonging to the genus *Glycyrrhiza* or a plant belonging to the genus *Medicago*, and further more preferably, *G. uralensis, G. glabra* or *M. truncatula*. The "plant" as used in the present invention includes a plant body, a plant organ, a plant tissue, a plant cell, cultured products of these plant parts, and a seed, and the "transformant" includes a transformed plant produced by genetic engineering and progeny thereof. A subject to be transformed is not particularly limited. Examples of a subject to be transformed include a plant body, a plant tissue (for example, an epidermis, a phloem, a parenchyma, a xylem, a vascular bundle), or a plant organ (for example, leave, petal, stem, root, or seed)), or plant cells.

A tumor tissue, a shoot, a hairy root, and the like, obtained as a result of transformation can be employed in cell culture, tissue culture, or organ culture in an intact state, or, they can be regenerated into a plant body by, for example, administration of an appropriate concentration of a plant hormone (for example, auxin, cytokinin, gibberellin, abscisic acid, ethylene, and brassinolide) and the like using a conventionally known plant tissue culture method. Regeneration of a plant body is generally conducted by differentiating a root on a medium in which appropriate kinds of auxin and cytokinin are mixed and transplanting it to a medium having a large amount of cytokinin to differentiate a shoot, and subsequently transplanting it to hormone-free soil.

Furthermore, it is possible to provide a transformant in which the polynucleotide described in Embodiment 2 or the recombinant vector described in Embodiment 3 are introduced so that they can be expressed and the expression of the polynucleotide is enhanced. Furthermore, it is possible to provide a transformant in which the expression of the polynucleotide described in Embodiment 2 is suppressed. Suppression of the expression of the polynucleotide includes suppression of transcription of the polynucleotide and suppression of translation into a protein, and it includes not only complete silencing of the expression but also partial suppression of the expression. The suppression of the expression of the polynucleotide may be carried out by artificial or natural mutation or destruction. The suppression of the expression of the polynucleotide by artificial mutation or destruction can be carried out by employing various genetic engineering techniques such as a RNA interference method, an antisense method, a ribozyme method, a co-suppression method, and a method to control a transcription factor.

According to the transformant of this embodiment, it is possible to provide a transformant in which the expression of the introduced polynucleotide is enhanced and thereby a production amount of glycyrrhizin is increased. Furthermore, by using the transformant in which the expression of the introduced polynucleotide is suppressed, a biosynthetic pathway of glycyrrhizin can be elucidated.

Embodiment 5

Embodiment 5 relates to a method for manufacturing a polynucleotide, which comprises culturing or growing the transformant of Embodiment 4, and extracting the polypeptide described in Embodiment 1 from the cultured product or the grown product.

When the polypeptide described in Embodiment 1 is produced by culturing a host, a medium suitable for culturing each host is used. As such media, media that are known in the technical field can be used. For example, although media are not limited, in general, when culturing is carried out by using a bacterium such as *Escherichia coli* as a host, an LB medium or an M9 medium is used. When culturing is carried out by using yeast as a host, a YPD medium, a YPG medium, a YPM medium, a YPDM medium, an SMM medium, and the like, are used. The medium appropriately contains a carbon source (for example, glucose, glycerin, mannitol, fructose, and lactose), a nitrogen source (for example, an inorganic nitrogen source such as ammonium sulfate and ammonium chloride, an organic nitrogen source such as a casein degradation product, a yeast extract, polypeptone, bacto tryptone, and a beef extract), inorganic salts (for example, diphosphate sodium, diphosphate potassium, magnesium chloride, magnesium sulfate, calcium chloride, and the like), vitamins (such as vitamin B1), and drugs (an antibiotic such as ampicillin, tetracycline, and kanamycin). Furthermore, media may include oleanane-type triterpene as a substrate of the polypeptide described in Embodiment 1, and preferably, β-amyrin, 11-oxo-β-amyrin, or 30-hydroxy-11-oxo-β-amyrin.

A culture condition is not particularly limited as long as it is suitable for expression of a polynucleotide, culturing is usually carried out at 10 to 45° C. for several hours to several hundred hours with aeration and stirring as needed. As to specific methods, see, for example, Sambrook, J. et. al. (1989) Molecular Cloning: a Laboratory Manual Second Ed., Cold Spring Harbor Laboratory Press, Cold Spring Harbor, N.Y.

In order to collect the polypeptide described in Embodiment 1 from a culture product (including a culture supernatant and a cultured transformant), a polypeptide accumulated in the culture product may be extracted by a known method, and then purified as needed. The polypeptide of interest can be obtained by, for example, employing a solvent extraction method, a salting-out method, a solvent precipitation method, a dialysis method, an ultrafiltration method, a gel electrophoresis method, a gel filtration chromatography, an ion exchange chromatography, a reverse phase chromatography, and an affinity chromatography, either alone or in combination thereof appropriately.

Note here that when the transformant is cultured in a medium into which oleanane-type triterpene such as the above-mentioned β-amyrin, preferably, β-amyrin, 11-oxo-β-amyrin, or 30-hydroxy-11-oxo-β-amyrin, which serves as a substrate for the polypeptide described in Embodiment 1, is added, a derivative in which carbon at the position 30 of the oleanane-type triterpene is oxidized (for example, 30-hydroxy-β-amyrin, or glycyrrhetinic acid) can be obtained.

When the polypeptide described in Embodiment 1 is produced by growing a transformed plant and the like, it is extracted from a regenerated plant body or the like by the above-described known methods, and purified as needed. Also, in a case of a plant belonging to the genus *Glycyrrhiza*, the polypeptide described in Embodiment 1 is contained in stolons and roots in abundance. Therefore, by collecting stolons and roots, the polypeptide described in Embodiment 1 can be obtained from such parts more efficiently.

According to the method for manufacturing the polynucleotide of this embodiment, a derivative in which carbon at the position 30 of the oleanane-type triterpene is oxidized or glycyrrhizin produced via a glycyrrhizin biosynthetic pathway can be obtained in abundance from a transformant of a plant in the family Fabaceae.

Embodiment 6

Embodiment 6 relates to a method for manufacturing glycyrrhetinic acid and 20-epi-glycyrrhetinic acid, the method comprising allowing the polypeptide described in Embodiment 1 and a polypeptide having an activity oxidizing carbon at the position 11 of oleanane-type triterpene to act on oleanane-type triterpene. As mentioned above, a biosynthetic pathway of glycyrrhizin after β-amyrin was not elucidated. However, according to the present invention, by combining the polypeptide described in Embodiment 1 with an enzyme that oxidizes carbon at the position 11 of oleanane-type triterpene, which had been previously isolated by the present inventors, it has become possible to produce glycyrrhetinic acid and 20-epi-glycyrrhetinic acid from β-amyrin for the first time. Glycyrrhetinic acid is a precursor of glycyrrhizin, and structurally corresponds to aglycone (sapogenin) of glycyrrhizin. Furthermore, 20-epi-glycyrrhetinic acid is one of isomers of glycyrrhetinic acid, and corresponds to aglycone of 20-epi-glycyrrhizin, which is one isomer of glycyrrhizin. 20-epi-glycyrrhizin is also pharmaceutically important material.

Examples of the "polypeptide having an activity of oxidizing carbon at the position 11 of oleanane-type triterpene" include (h) a polypeptide (an amino acid sequence is shown in SEQ ID NO: 16) encoded by a cytochrome P450 type enzyme gene CYP88D6 (GenBank Accession No. AB433179; the nucleic acid sequence is shown in SEQ ID NO: 15) (Patent Literature 2). Alternatively, it may be (i) a polypeptide having an amino acid sequence comprising deletion, substitution, or addition of one or several amino acids in the amino acid sequence shown in SEQ ID NO: 16 and having an activity of oxidizing carbon at the position 11 of oleanane-type triterpene, and (j) a polypeptide having an amino acid sequence having 80% or more identity with the amino acid sequence shown in SEQ ID NO: 16 and having an activity of oxidizing carbon at the position 11 of oleanane-type triterpene. Alternatively, it may be (k) a polypeptide encoded by a nucleotide sequence comprising deletion, substitution, or addition of one or several nucleotides in the nucleotide sequence shown in SEQ ID NO: 15, a nucleotide sequence having 80% or more identity with the nucleotide sequence shown in SEQ ID NO: 15, or a nucleotide sequence hybridizing the nucleotide sequence complementary to the nucleotide sequence shown in SEQ ID NO: 15 under stringent conditions. Furthermore, fragments of the polypeptide in the above-mentioned (h) to (k) having an activity of oxidizing carbon at the position 11 of oleanane-type triterpene can be employed.

The oleanane-type triterpene that serves as a substrate in this embodiment may substantially be oleanane-type triterpene described in Embodiment 1. It is preferably β-amyrin, 11-oxo-β-amyrin, or 30-hydroxy-β-amyrin.

The present invention can be carried out in vitro and/or in vivo. When the present invention is carried out in vitro, the above-mentioned two polypeptides may be reacted with oleanane-type triterpene that serves as a substrate in a reaction buffer. The composition of the reaction buffer is not particularly limited as long as it contains an electron donator such as NADPH, and it has a pH and a salt concentration that are in the range of the optimum activity conditions of the above-mentioned two polypeptides. For example, 1 M phosphate-potassium buffer (pH 7.2) into which an electron donator such as NADPH is added can be used. When the present invention is carried out in vivo, for example, an expression vector in which a polynucleotide encoding the above-mentioned two polypeptides, that is, polynucleotide described in Embodiment 2, as well as polynucleotide encoding a polypeptide having an activity of oxidizing carbon at the position 11 of oleanane-type triterpene, and fragments thereof may be introduced in an appropriate host (organism or bacteria). Alternatively, one or both of these polypeptides can be directly provided in the host. The host is not particularly limited as long as an introduced polynucleotide can be expressed and/or provided polypeptide can function in the host. Examples include bacteria (for example, *Escherichia coli*, or *Bacillus subtilis*), yeast (for example, *Saccharomyces cerevisiae, Schizosaccharomyces pombe*, or *Pichia pastoris*), a fungus (for example, *Aspergillus, Neurospora, Fuzarium*, or *Trichoderma*), a monocotyledonous plant (for example, Gramineae), or a dicotyledonous plant (for example, Fabaceae, or Brassicaceae), or a plant cell (including plant tissue and plant organ), an animal cell, or an insect cell (for example, sf9 or sf21). Preferably, a yeast, a fungus, a monocotyledonous plant, a dicotyledonous plant, or a plant cell is used. More preferably, a plant in the family Fabaceae is used. Further more preferably, a plant in the subfamily Faboideae, for example, a plant belonging to the genus *Arachis*, a plant belonging to the genus *Cicer*, a plant belonging to the genus *Aspalathus*, a plant belonging to the genus *Dalbergia*, a plant belonging to the genus *Pterocarpus*, a plant belonging to the genus *Desmodium*, a plant belonging to the genus *Lespedeza*, a plant belonging to the genus *Uraria*, plants belonging to the tribe Galegeae, a plant belonging to the genus *Astragalus*, plants belonging to the genus *Glycyrrhiza*, a plant belonging to the genus *Oxytropis*, a plant belonging to the genus *Augyrocytisus*, a plant belonging to the genus *Cytisus*, a plant belonging to the genus *Genista*, a plant belonging to the genus *Spartium*, a plant belonging to the genus *Hedysarum*, a plant belonging to the genus *Cyamopsis*, a plant belonging to the genus *Indigofera*, a plant belonging to the genus *Lotus*, a plant belonging to the genus *Lupinus*, a plant belonging to the genus *Wisteria*, a plant belonging to the genus *Cajanus*, a plant belonging to the genus *Canavalia*, a plant belonging to the genus *Erythrina*, a plant belonging to the genus *Glycine*, a plant belonging to the genus *Hardenbergia*, a plant belonging to the genus *Lablab*, a plant belonging to the genus *Mucuna*, a plant belonging to the genus *Phaseolus*, a plant belonging to the genus *Psophocarpus*, a plant belonging to the genus *Pueraria*, a plant belonging to the genus *Vigna*, a plant belonging to the genus *Robinia*, a plant belonging to the genus *Castanospermum*, a plant belonging to the genus *Maackia*, a plant belonging to the genus *Ormosia*, a plant belonging to the genus *Sophora*, a plant belonging to the genus *Styphnolobium*, a plant belonging to the genus *Medicago*, a plant belonging to the genus *Trigonella*, a plant belonging to the genus *Trifolium*, a plant belonging to the genus *Lathyrus*, a plant belonging to the genus *Lens*, a plant belonging to the genus *Pisum* and a plant belonging to the genus *Vicia*. Particularly preferably, it is a plant belonging to the genus *Glycyrrhiza* or a plant belonging to the genus *Medicago*. Further more preferably, it is *G. uralensis, G. glabra* or *M. truncatula*.

When the above-mentioned host cannot biosynthesize the oleanane-type triterpene that serves as a substrate, one or more appropriate polynucleotide encoding the oleanane-type triterpene synthase or the fragment thereof can be introduced into the host so that the host can biosynthesize the substrate. Alternatively, a substrate may be directly imparted to the host. As a gene encoding an enzyme that synthesizes the substrate, for example, β-amyrin synthase can be employed (for example, OSC1). By placing a transformant having an expression vector in which the above-mentioned two polynucleotides of the present invention, and, if necessary, a polynucleotide encoding the substrate synthase or the fragment thereof are introduced in appropriate expression inducing conditions, glycyrrhetinic acid and 20-epi-glycyrrhetinic acid are produced in the host. Specifically, in the case of using yeast as a host, the yeast cannot biosynthesize β-amyrin that serves as a substrate. Thus, the yeast is transformed with an expression vector and the like into which a gene encoding β-amyrin synthase of an appropriate organism species is introduced together with an expression vector into which the polynucleotide of the present invention is introduced, and then used. Thereby, the present invention can be achieved. See, the below-mentioned Example 22.

Furthermore, expression of the above-mentioned two polynucleotides, and, if necessary, a polynucleotide encoding the substrate synthase or the fragment thereof may be regulated (enhanced or suppressed) independently or coordinately. The independent regulation of expression can be achieved by, for example, connecting the polynucleotide to a promoter having a different induction condition, or connecting it to a promoter having different expression strength. The coordinate regulation of expression can be achieved by, for example, connecting each polynucleotide to the same kind of promoter. Besides, by using technique described in the above-mentioned Embodiment 4, expression of each polynucleotide may be regulated.

According to the manufacturing method of this embodiment, in a plant belonging to the genus *Glycyrrhiza* and the like, glycyrrhetinic acid and 20-epi-glycyrrhetinic acid that are precursors of glycyrrhizin and 20-epi-glycyrrhizin can be produced from β-amyrin stably and continuously.

Furthermore, according to the manufacturing method of this embodiment, production of glycyrrhetinic acid and 20-epi-glycyrrhetinic acid in a host can be regulated.

Furthermore, according to the manufacturing method of this embodiment, glycyrrhetinic acid and 20-epi-glycyrrhetinic acid can be biosynthesized even in organism species or organism cells which originally cannot biosynthesize glycyrrhetinic acid and 20-epi-glycyrrhetinic acid. Therefore, by carrying out biosynthesis in a host such as yeast that is easily cultured and has high proliferation potency, glycyrrhetinic acid and 20-epi-glycyrrhetinic acid can be produced in abundance stably and at low cost. Conventionally, glycyrrhetinic acid and 20-epi-glycyrrhetinic acid were extracted from a plant body such as *Glycyrrhiza*, and were not available from other methods, and therefore they were expensive. However, according to the manufacturing method of this embodiment, they can be provided at low cost.

Embodiment 7

Embodiment 7 relates to a plant selection method using a polynucleotide described in Embodiment 2. The method selects the plant by determining the presence or absence or expression of the polynucleotide described in Embodiment 2 in plants. The method comprises detecting or quantitating the polynucleotide by carrying out a nucleic acid amplification method or a nucleic acid hybridization of a sample containing a nucleic acid prepared from the aforementioned plant using the polynucleotide or the fragment thereof.

The sample containing a nucleic acid can be prepared by using known methods in this technical field, for example, a phenol extraction method, a phenol-chloroform extraction method, a CTAB method, and the like.

The above-mentioned "nucleic acid amplification method" is a method of amplifying a certain nucleic acid region by nucleic acid polymerase. Examples of such methods include a PCR (polymerase chain reaction) method, an RT-PCR (reverse transcription polymerase chain reaction) method, an ICAN (Isothermal and Chimeric primer-initiated Amplification of Nucleic acids) method, or methods applying them (for example, a real-time PCR method). Preferable method is a PCR method. This is because the method is the most widely used in the technical field all over the world at present, and reagents, kits, and reaction devices, and the like, for this method are sufficiently available, and various applied technologies are known.

The "nucleic acid hybridization method" is a method for detecting or quantitating a polynucleotide of interest or a fragment thereof by using a nucleic acid fragment having a nucleotide sequence complementary to a nucleotide sequence of the polynucleotide of interest or the fragment thereof, and by using base pairing between the polynucleotide of interest or the fragment thereof and the nucleic acid fragment. Examples of a nucleic acid hybridization method include, for example, a DNA-DNA hybridization method, a DNA-RNA hybridization method, or a RNA-RNA hybridization method. As to the specific methods of these methods, see, for example, Northern hybridization ("Bunshiseibutsugaku jikken protocol I (Short Protocols in Molecular Biology I)" (1997), joint transition by Nishino and Sano, Maruzen Co., Ltd.), and a DNA microarray method (see "DNA microarray to saishin PCR ho (DNA microarray and the latest PCR method)" (2000), edited by Muramatsu and Nawa, Shujunsha Co., Ltd.), and the like.

A primer or a probe used in the nucleic acid amplification method or the nucleic acid hybridization may be designed based on any of the nucleotide sequences shown in Embodiment 2, preferably a nucleotide sequences shown in SEQ ID NO: 4 or 14, or a nucleotide sequence of a variant or an orthologous gene thereof. A nucleic acid constituting the primer and/or the probe of the present invention is generally DNA or RNA. However, if necessary, the nucleic acid may include chemically modified nucleic acid or pseudo nucleic acid, for example, PNA (Peptide Nucleic Acid), LNA (Locked Nucleic Acid; registered trademark), methyl phosphonate DNA, phosphorothioate DNA, 2'-O-methyl RNA, and the like, or the combination thereof. Furthermore, the primer and the probe may be modified or labeled by using fluorescent dye (for example, fluorescamine or a derivative thereof, rhodamine or a derivative thereof, FITC, cy3, cy5, FAM, HEX, VIC), a modulation material such as a quencher agent (TAMRA, DABCYL, BHQ-1, BHQ-2, or BHQ-3), biotin or (strepto-)avidin, magnetic beads, or the like, or an isotope (for example, $^{32}P$, $^{33}P$, $^{35}S$). Modification/labeling position of the modulation material and the like in the primer or the probe may be appropriately determined in accordance with the properties of the modulation material or purpose of use. In general, 5' or 3' terminal portion is often modified. Furthermore, one primer and probe molecule may be modified by one or more modulation materials, or the like.

The size of a primer and a probe to be used in the present invention are not particularly limited, but in a case of a primer, the size is usually about 15 to about 50 nucleotides long, and preferably about 17 to about 30 nucleotides long. In a case of a probe, if it is used for Southern or Northern hybridization, the size is at least about 10 nucleotides long or more to full length, preferably about 15 nucleotides long or more to full length, more preferably, about 30 nucleotides long or more to full length, and further more preferably about 50 nucleotides long or more to full length. If a probe is used for DNA microarray, the length is about 10 to about 50 nucleotides long, preferably about 15 to about 30 nucleotides long, and more preferably about 20 to about 25 nucleotides long. However, the size is not limited thereto. In general, as a probe is longer, the hybridization efficiency is increased and sensitivity is increased. On the other hand, as a probe is shorter, the sensitivity is reduced but, on the contrary, specificity is increased. For a probe on the solid phase, 0.1 µg to 0.5 µg is generally spotted in a solution. As specific examples of the primer and probe, for example, for a primer, SEQ ID NOs: 1 and 2 can be used.

Conditions of the nucleic acid amplification vary depending upon the nucleotide length and amount of nucleic acid fragment to be amplified, as well as the nucleotides length and Tm value and the like of a primer to be used, and therefore they are appropriately determined according to these conditions. For example, conditions of PCR method generally include carrying out denaturation at 94 to 95° C. for five seconds to five minutes, annealing reaction at 50 to 70° C. for ten seconds to one minute, and elongation reaction at 68 to 72° C. for 30 seconds to three minutes, which are carried out as one cycle. This cycle is carried out for about 15 to 40 cycles, followed by final elongation reaction at 68 to 72° C. for 30 seconds to 10 minutes.

A nucleic acid amplification product can be detected by using, for example, agarose electrophoresis, polyacrylamide gel electrophoresis, dot hybridization, or the like. Furthermore, the quantification of these nucleic acid amplification products can be carried out by using Chemilumi-Imaging Analyzer (for example, ATTO Corporation: Light Capture Series), and Imaging Analyzer (for example, FUJIFILM: BAS Series).

An example of a method for quantitating an expression level of the polynucleotide described in Embodiment 2 by a PCR method includes a RT-PCR method employing an internal standard substance (see "PCR ho saizensen (Forefront of PCR Method)" (1996), edited by Sekiya and Fujinaga, Kyoritsu Shuppan Co., Ltd). A housekeeping gene (for example, GAPDH, β-actin) is generally employed as an internal standard to be used. In this method, a relative result with respect to an internal standard sample of the target mRNA amount is obtained. While a PCR reaction is conducted on one sample, a reaction liquid is sampled every several cycles to quantitate an amount of PCR product, and obtained values are plotted on a graph. A regression analysis is performed with respect to points in an exponential amplification phase on the graph thus obtained to find y-intercept, thereby an initial amount of a template can be calculated ("Bio jikken illustrated (Biological Experiment Illustrated) 3", "honto ni fueru PCR (truly productive PCR)" (1998), written by Nakayama, H., Shujunsha Co., Ltd.)

Furthermore, an expression amount of the polynucleotide described in Embodiment 2 can be quantitated by a real-time quantitative PCR method. When a PCR reaction is carried out in a reaction system in which a PCR product is specifically fluorescently-labeled by using a thermal cycler instrument equipped with a device which detects a fluorescence intensity, an amount of a product in the reaction can be monitored in real time without requiring sampling, and results thus obtained can be subjected to regression analysis on a computer. Examples of a method for labeling a PCR product include a method employing a fluorescently-labeled probe (for example, a TaqMan (registered trademark) PCR method) and a method employing a reagent that specifically binds to a double-stranded DNA. The TaqMan (registered trademark) PCR method uses a probe whose 5'-terminal is modified with a quencher agent and 3'-terminal is modified with a fluorescent. In general, the quencher agent at 5'-terminal suppresses the fluorescent dye at 3'-terminal. However, once a PCR reaction is conducted, a probe is degraded by a 5'→3' exonuclease activity of a Taq polymerase and then the suppression by the quencher agent is cancelled to emit florescence. The amount of fluorescence reflects an amount of a PCR product. Since the number of cycle (CT) when a PCR product reaches a detection limit and an initial amount of a template are inversely correlated, an initial amount of a template is quantitated by measuring CT in a real-time measurement method. If CT is measured using multiple levels of known amounts of templates and a calibration curve is produced, an absolute value of an initial amount of a template of an unknown sample can be calculated. Examples of reverse transcriptase used in a RT-PCR include, for example, M-MLV RTase and ExScript RTase (TaKaRa), and Super Script II RT (GIBCO-BRL).

When nucleic acid hybridization is carried out, not only the above-mentioned probe but also a nucleic acid in a sample may be modified/labeled. For modification/labeling, isotope (for example, $^{32}P$, $^{33}P$, $^{35}S$) or fluorescence (fluorescamine or a derivative thereof, rhodamine or a derivative thereof, FITC, Cy3, or Cy5) can be used. An appropriate modification/labeling may be carried out depending upon the purpose, and not particularly limited.

It is preferable that hybridization is carried out under stringent conditions mentioned above for excluding non-objective non-specifically hybridized nucleic acids.

A Northern hybridization method is generally used for detection and quantitation of a RNA sequence. A RNA sample obtained from a plant by a known method is subjected to agarose gel electrophoresis to be separated, and subsequently the RNA thus separated is transferred to a nylon or nitrocellulose membrane. Then, the polynucleotide described in Embodiment 2 is subjected to hybridization using labeled cDNA or a fragment thereof as a probe so as to detect or quantitate the polynucleotide of interest.

In a DNA microarray method, cDNA encoding the polynucleotide of the present invention, or a sense strand or an antisense strand, or fragments thereof is immobilized as a probe on an array on a glass, a filter or the like. A reverse transcription reaction is carried out on RNA obtained by a known method, and Cy3-dUTP, Cy5-dUTP, and the like, are allowed to be taken up, thereby labeled cDNA is obtained. Then, hybridization of the probe immobilized on an array with the labeled cDNA is carried out so as to detect and quantitate the polynucleotide of the present invention. A plant with a high content of glycyrrhizin can be thus selected and screened.

Note here that for the specific methods and the like related to the above-mentioned molecular biological techniques, see Sambrook, J. et. al., (1989) Molecular Cloning: a Laboratory Manual Second Ed., Cold Spring Harbor Laboratory Press, Cold Spring Harbor, N.Y.

EXAMPLES

Hereinafter, the present invention is described specifically based on Examples. However, these Examples are not intended to limit the present invention.

Example 1

Preparation of mRNA from Plant Belonging to the Genus *Glycyrrhiza* and Production of cDNA Library (1)

A stolon of seven-year-old *G. uralensis* cultivated in a field at Research Center for Medicinal Plant Resources, Hokkaido Division (Nayoro city, Hokkaido) of National Institute of Biomedical Innovation was harvested in June. A total RNA was prepared therefrom using a RNA extraction reagent, RNAwiz™ (Ambion, Inc.) according to the attached protocol. From the obtained total RNA, mRNA was prepared, and then cDNA was synthesized by a vector-capping method (Kato, S. et al., DNA Res., 12, 53-62, 2005). Then, the cDNA fragments were incorporated into a plasmid vector pGCAPzf3 (Tsugane, T. et al., Plant Biotechnology., 22, 161-165, 2005), thereby constructing a cDNA library.

Example 2

Preparation of mRNA from Plant Belonging to Genus *Glycyrrhiza* and Production of cDNA Library (2)

A stolon of *G. uralensis*, presumed to have been cultivated in a field for four years or longer after a transplant in a field at Research Center for Medicinal Plant Resources, Tsukuba Division (Tsukuba city, Ibaraki) of National Institute of Biomedical Innovation, was harvested in October. A total RNA was prepared by using a RNA extraction reagent TRIzol (registered trademark) (Invitrogen Corporation) and a purification column RNeasy (registered trademark) (Qiagen) according to the attached protocols. From the total RNA thus obtained, mRNA was prepared, and then cDNA was synthesized by an oligo-capping method (Murayama, K. et al., Gene, 138, 171-174, 1994, and Suzuki, Y. et al., Gene, 200, 149-156). Then, the cDNA fragments thus obtained were incorporated into a plasmid vector pCMVFL3, thereby constructing a cDNA library.

Example 3

Sequence Analysis (1)

A strain of *Escherichia coli*, DH12S (Invitrogen Corporation), or DH10B T1 Phage-Resistant (Invitrogen Corporation) was transformed with the cDNA library obtained in Example 1, and approximately 30,000 single colonies thus obtained were picked up and inoculated on 384 plates. DNA to be used as a template in a sequencing reaction was amplified by a colony PCR, and the DNA thus amplified was purified by ethanol precipitation. Using the DNA thus purified as a template, sequencing reaction was carried out from a 5' terminal side of each cDNA fragment with BigDye ver 3.1, a product of Applied Biosystems. Following purification with ethanol precipitation, nucleotide sequences were analyzed by 3730×1 DNA Analyzer, a product of Applied Biosystems.

Example 4

Sequence Analysis (2)

A strain of *Escherichia coli*, DH5α was transformed with the cDNA library obtained in Example 2, and approximately 26,000 single colonies thus obtained were picked up and inoculated on 384 plates. DNA to be used as a template in a sequencing reaction was amplified by a colony PCR, and the DNA thus amplified was purified by ethanol precipitation. Using the DNA thus purified as a template, sequencing reactions were carried out from a 5' terminal side of each cDNA fragment with BigDye ver 3.1, a product of Applied Biosystems. Following purification with ethanol precipitation, nucleotide sequences were analyzed by 3730×1 DNA Analyzer (a product of Applied Biosystems).

Example 5

Clustering of EST (Expression Sequence Tag)

Approximately 30,000 EST data obtained in Example 3 and approximately 26,000 EST data obtained in Example 4 were integrated into one set of data, and clustering was carried out by using a PHRAP program. As a result, 10,372 unique contigs were obtained.

Example 6

Extraction of Cytochrome P450 Gene Through Homology Search

A BLASTX search was carried out (Altschul, S. F. et al., Nucleic Acids Res. 25, 3389-3402, 1997) with respect to known proteins registered in a database of NCBI (National Center for Biotechnology Information) using 10,372 contig sequences obtained in Example 5 as queries. The present inventors predicted that cytochrome P450 oxidase was involved in glycyrrhizin biosynthetic pathway after β-amyrin, and contigs having a high homology to known cytochrome P450 oxidase registered in the database were selected. Among a plurality of EST clones constructing the selected contigs, plasmid DNA was prepared for a clone determined to retain a longest 5' terminal region, and full-length nucleotide sequences of each of cloned cDNA fragment (36 fragments) was determined.

Example 7

Gene Expression Analysis (Screening of Candidate Gene)

In order to select a molecular species which is highly likely to be involved in biosynthesis of glycyrrhizin from the group of 36 cytochrome P450 genes obtained in Example 6, the organ in the plant body in which each cytochrome P450 molecular species was expressed was examined using a RT-PCR method.

A total RNA was prepared from a total of four kinds of different plant tissues including an underground tissue (a thickened root and a stolon) where glycyrrhizin is highly accumulated and an aboveground tissue (a leave and a steam) where glycyrrhizin is not detected. Using 1 μg of the obtained total RNA, a first-strand cDNA synthesis was carried out using a SMART RACE cDNA amplification kit (Clontech Laboratories) according to the attached protocol.

Subsequently, sense primers and antisense primers specifically annealing to each cytochrome P450 gene were designed, and PCR was carried out for 25 to 30 cycles using Ex Taq™ DNA polymerase (TaKaRa) using 2 μl each of four kinds of first strand cDNA as templates. The PCR fragments thus obtained were analyzed by agarose gel electrophoresis (FIG. 1b). Cytochrome P450 molecular species highly expressing in roots and stolons was selected. Among them, for cytochrome P450 molecular species (GuCYP72.1) which had been confirmed to have an enzymatic activity of oxidizing triterpene, the following Examples were carried out.

Example 8

Amplification and Cloning to Entry Vector of Full Length Coding Region of GuCYP72.1

Using a plasmid clone comprising a full length coding region of GuCYP72.1 (produced by using pGCAPzf3) as a template, PCR was carried out for 30 cycles at an annealing temperature of 55° C. using a Pfu-Turbo DNA Polymerase (Stratagene), using oligo DNA of the sites corresponding to the N-terminal and C-terminal of GuCYP72.1 polypeptide as primers (SEQ ID NOs: 1 and 2). Four nucleotides (cacc) are attached to the 5'-terminal of the primer of SEQ ID NO: 1, which are necessary for cloning in an entry vector pENTR™/D-TOPO (registered trademark) (Invitrogen Corporation). DNA fragments amplified by the PCR were cloned to pENTR™/D-TOPO (registered trademark) entry vectors, and the nucleotide sequences of the four independent clones thus obtained were determined. The nucleotide sequence of the polynucleotide thus obtained is SEQ ID NO: 3, and polypeptide sequence predicted therefrom is SEQ ID NO: 4.

Example 9

Construction of Expression Vector for Protein of the Present Invention Using Baculovirus-Insect Cell Expression System A plasmid comprising the polynucleotide shown in SEQ ID NO: 3 produced in Example 8 (an entry clone) and a destination vector pDEST™ 8 (Invitrogen Corporation) were mixed with each other, and the polynucleotide shown in SEQ ID NO: 3 was transferred to the pDEST™ 8 vector by a nucleotide sequence-specific recombination reaction (GATEWAY™ attLxattR reaction), thereby an insect cell expression construct was constructed. A strain of *Escherichia coli*, DH10Bac (Invitrogen Corporation) was transformed with the construct thus obtained by a calcium chloride method. Bacmid DNA (a primary recombinant baculovirus) was prepared from transformant colonies according to the attached protocol.

Example 10

Expression of Protein of the Present Invention by Baculovirus-Insect Cell Expression System Using an ordinary method (Invitrogen Corporation, Bac-to-Bac Baculovirus Expression System, catalog number 10359016) according to the attached protocol, the Bacmid DNA produced in Example 9 was allowed to infect and replicate in insect cells (*Spodoptera frugiperda* 9), and then a purified virus liquid with a high titer (the titer=approximately $1\times10^8$ pfu/ml) was prepared. In 3 ml of Grace's Insect Cell Culture Medium (GIBCO BRL), $1.0\times10^6$ insect cells were suspended, to which 30 μl of the high titer virus liquid was added. The mixture was incubated at room temperature for 30 minutes. To the mixture, 50 ml of Grace's Insect Cell Culture Medium (containing aminolevulinic acid with a final concentration of 100 μM, a fetal bovine serum with a final concentration of 10%, ferric citrate with a final concentration of 100 μM, and Pluronic F68 with a final concentration of 0.1%) was added. The mixture was then transferred to a 300 ml-flask and cultured at 27° C. at 150 rpm for 96 hours.

Example 11

Preparation of Microsomal Fraction from Insect Cell

The insect cell culture solution (50 ml) obtained in Example 10 was centrifuged at 2,330 g for five minutes at 4° C. to collect the insect cells. The insect cells were washed with ice-cold phosphate buffer three times and then suspended in 5 ml of 50 mM phosphate-potassium buffer (pH 7.2, containing 1 mM EDTA, 1 mM DTT, and 20% Glycerol). The cells were disrupted by sonication by using BRANSON SONIFER 250 (BRANSON), followed by centrifugation at 2,330 g at 4° C. for 20 min. A supernatant was collected and centrifuged at 100,000 g at 4° C. for one hour. The obtained pellets (microsomal fraction) were suspended in 2 ml of 50 mM phosphate-potassium buffer (pH 7.2, containing 1 mM EDTA, 1 mM DTT, and 20% Glycerol).

Example 12

Preparation of Substrate Triterpene

Figure 2:
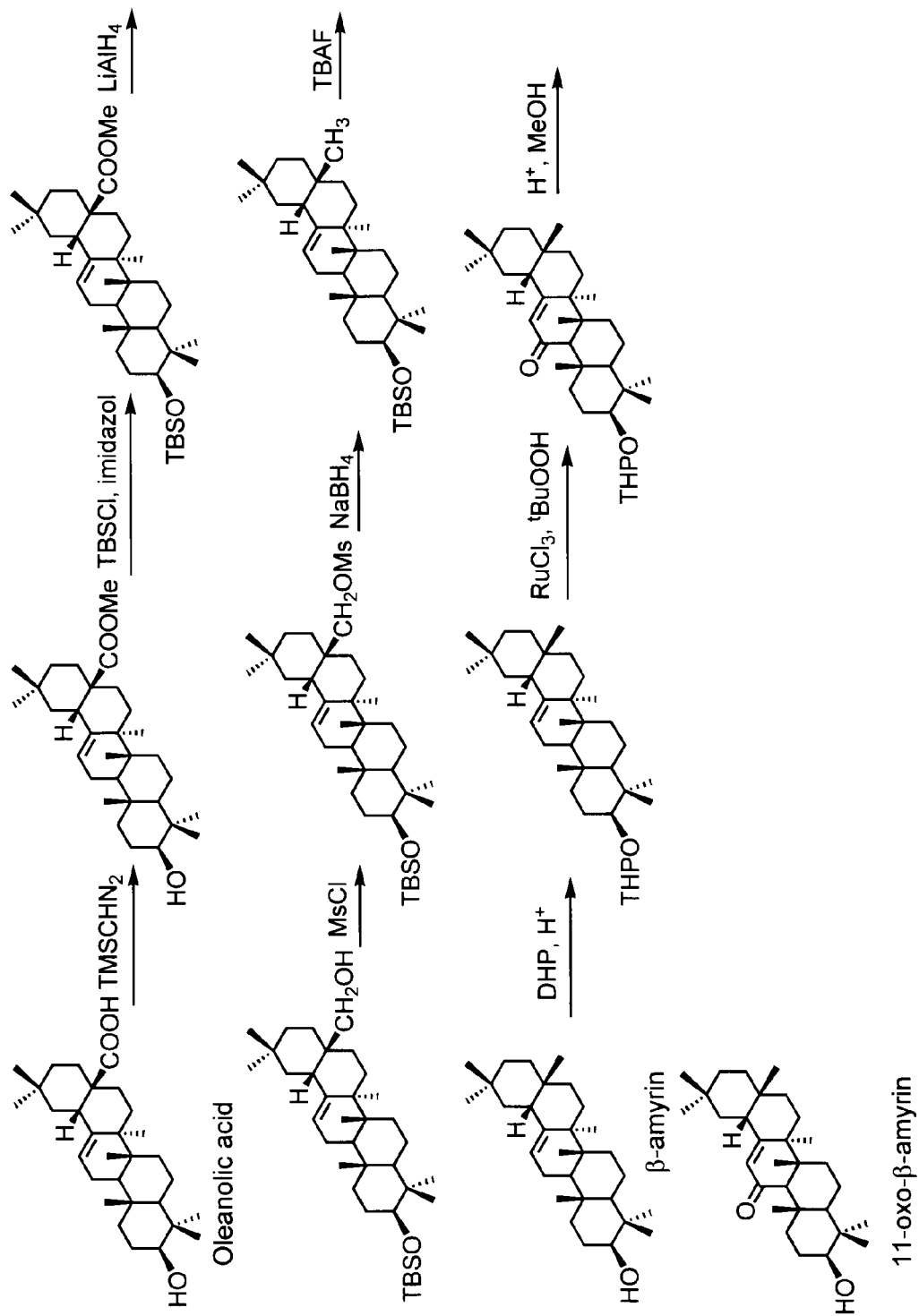
FIG. 2 shows a method for synthesizing triterpene.
Figure 3:
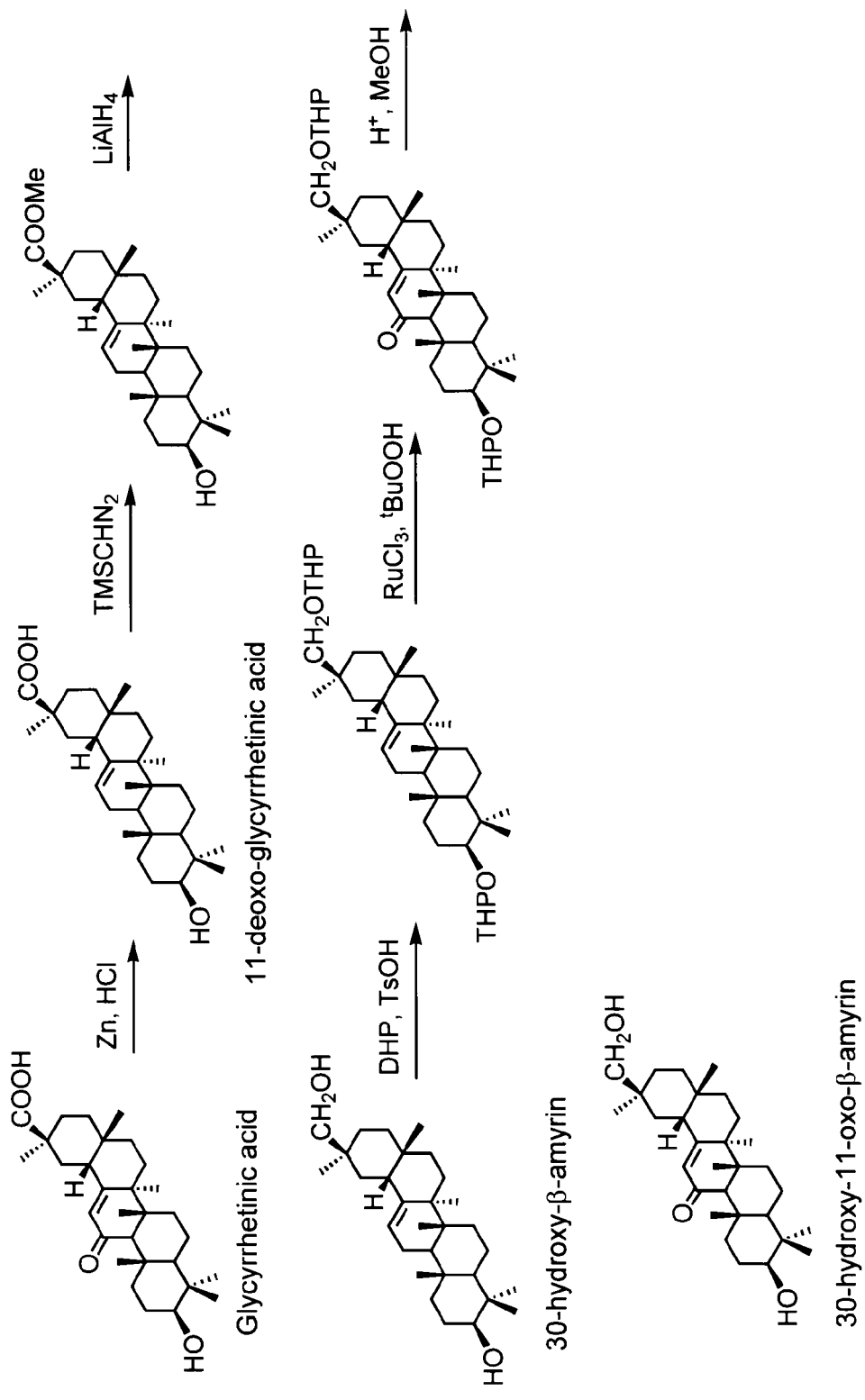
FIG. 3 shows a method for synthesizing triterpene.

A triterpene serving as a substrate to be used for testing the activity of the microsomal fraction obtained in Example 11 was synthesized by methods shown in FIGS. 2 and 3.

(1) β-amyrin

Oleanolic acid (SIGMA) was reacted with trimethylsilyldiazomethane to convert a carboxylic acid into a methyl ester and to protect a hydroxyl group as a tert-butyldimethylsilyl group. The methyl ester was reduced to an alcohol, on which mesyl chloride was acted to obtain a mesyl ester, which was then converted into a methyl by a reductive substitution reaction. The methyl was deprotected to provide β-amyrin. A structure thereof was determined by analyzing $^1$H-NMR and $^{13}$C-NMR spectra.

(2) 11-oxo-β-amyrin

A hydroxyl group at the position 3 of β-amyrin was protected with a tetrahydropyranyl group, and ruthenium chloride and tert-butyl hydroperoxide were allowed to act thereon to convert a methylene carbon at the position 11 into a carbonyl group, followed by deprotecting to give 11-oxo-β-amyrin. A structure thereof was determined by analyzing $^1$H-NMR and $^{13}$C-NMR spectra.

(3) 11-deoxoglycyrrhetinic acid

Zinc and hydrochloric acid were allowed to act on glycyrrhetinic acid (SIGMA) to reduce a carbonyl group at the position 11. Thus, 11-deoxoglycyrrhetinic acid was obtained. A structure thereof was determined by analyzing $^1$H-NMR and $^{13}$C-NMR spectra.

(4) 30-hydroxy-β-amyrin

Trimethylsilyldiazomethane was allowed to act on 11-deoxoglycyrrhetinic acid to lead a carboxylic acid to a methyl ester, and then the ester was reduced to obtain 30-hydroxy-β-amyrin. A structure thereof was determined by analyzing $^1$H-NMR and $^{13}$C-NMR spectra.

(5) 30-hydroxy-11-oxo-β-amyrin

A hydroxyl group of 30-hydroxy-β-amyrin was protected as a tetrahydropyranyl group, and ruthenium chloride and tert-butyl hydroperoxide were allowed to act thereon to convert a methylene carbon at the position 11 into a carbonyl group, followed by deprotecting to give 30-hydroxy-11-oxo-β-amyrin. A structure thereof was determined by analyzing $^1$H-NMR and $^{13}$C-NMR spectra.

Example 13

In Vitro Assay Using Microsomal Fraction

After mixing 50 µl of the microsomal fraction obtained in Example 11, 25 µl of 1M phosphate-potassium buffer (pH 7.2), 1 µl (a final concentration of 0.1 unit/ml) of purified cytochrome P450 reductase derived from *Arabidopsis thaliana* (Mizutani, M. and Ohta, D, Plant Physiol, 116, 357-367, 1998), 25 µl (a final concentration of 1 mM) of NADPH, 5 µl (a final concentration of 20 µM) of reaction substrate (11-oxo-β-amyrin), and 394 µl of sterilized water, the obtained mixture was incubated at 30° C. while stirring at 1,000 rpm for two hours.

Example 14

Identification of Converted Product

The reaction solution obtained in Example 13 was extracted on ethyl acetate. Then, a solvent was removed by drying from the ethyl acetate part. Subsequently, N-methyl-N-(trimethylsilyl)trifluoroacetamide was added thereto and the mixture was heated at 80° C. for 30 minutes to be derivatized into trimethylsilyl ether, thereby a sample for a GC-MS analysis was provided. Automass (JEOL)-6890N (Agilent technologies) was used for GC-MS, and HP-5 column (J&W Scientific Inc.; 0.32 mm×30 m; 0.25 mm film thickness) was used for a column to analyze converted products. Identity of the converted products was determined by comparison with respect to the GC retention time and the MS spectra by using a substrate triterpene prepared in Example 12 as an authentic sample.

Herein, enzymatic assay using the microsome prepared from an insect cell expressing the polypeptide (GuCYP72.1) shown in SEQ ID NO: 4 was carried out. As a result, three peaks (black arrow in FIG. 4) that 11-oxo-β-amyrin provided as a substrate (void arrow A in FIG. 4) was presumably hydroxylated were detected. Among them, the retention time and the mass spectrum of a peak shown by B correspond well to 30-hydroxy-11-oxo-β-amyrin. These peaks were not detected in the similar experiment using a microsomal fraction (negative control) derived from an insert cell into which an empty vector had been introduced.

Figure 4:
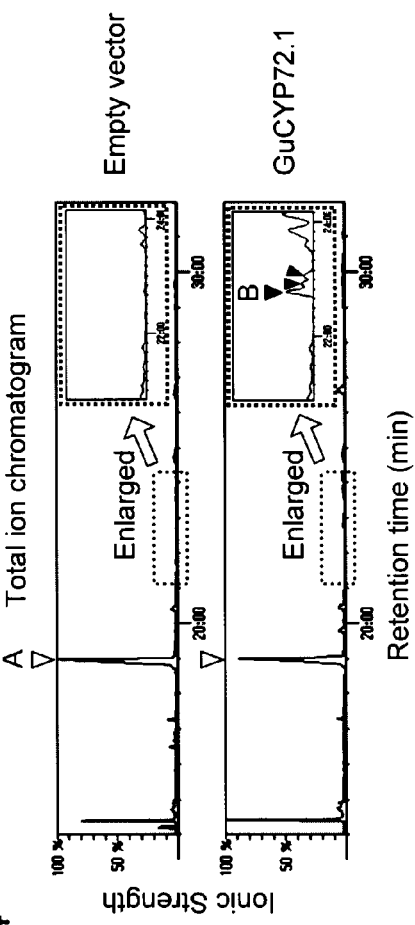
FIG. 4 shows a result of detection of a converted product of 11-oxo-β-amyrin by polypeptide of the present invention, and also shows the position of catalysis by the polypeptide in a presumable biosynthetic pathway from β-amyrin to glycyrrhizin.
Figure 4:
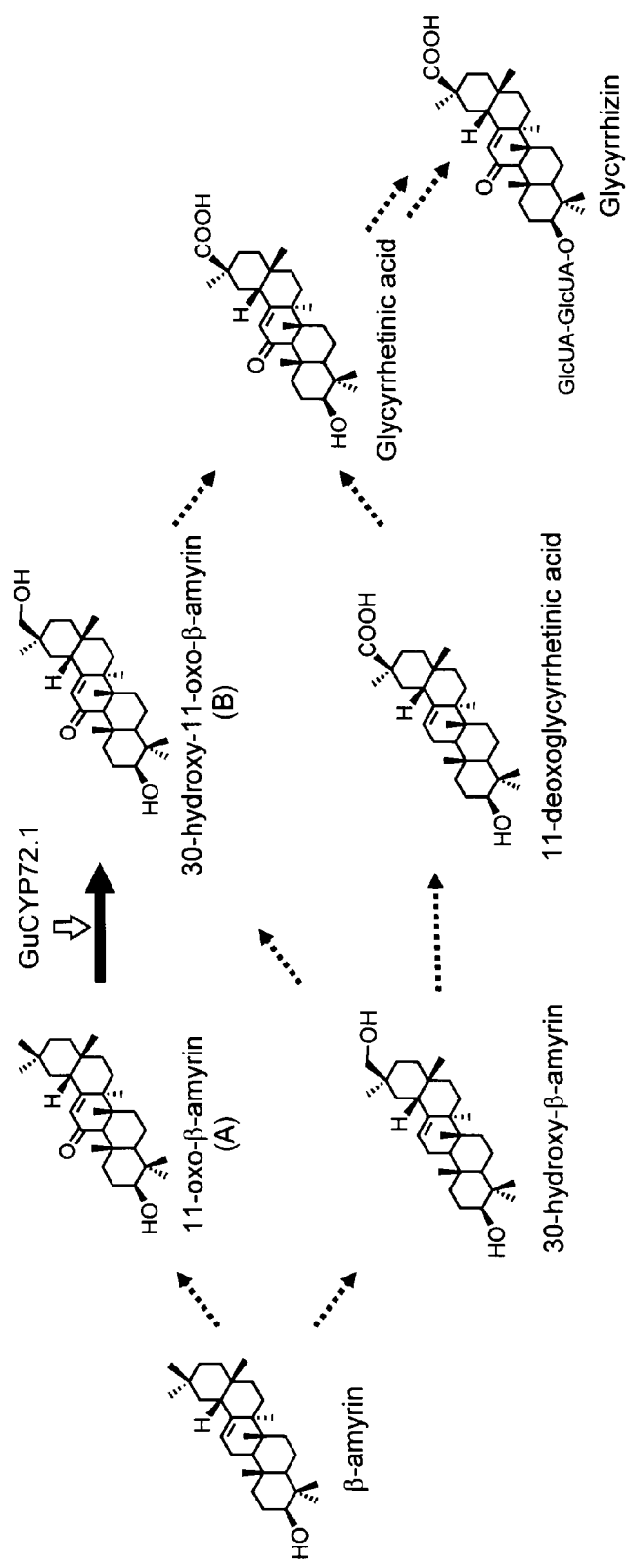

From the above-mentioned results, an enzyme (GuCYP72.1) involved in hydroxylation reaction at the position 30 of glycyrrhizin, which was thought to be involved in biosynthesis, was identified for the first time (FIG. 4).

Example 15

Construction of Yeast Expression Vector pYES3-ADH-OSC1 for cDNA of *Lotus* β-Amyrin Synthase (OSC1) Gene By using *Lotus* (*Lotus japonicus*), whose EST and genome analysis are being carried out as a model plant of the family Fabaceae, a yeast expression vector for a β-amyrin synthase (OSC1) gene was constructed.

A plasmid in which cDNA of *Lotus* OSC1 gene was introduced (Sawai et al. (2006) Plant Sci 170: 247-257) was digested with KpnI and XbaI to cleave out OSC1 cDNA region. Similarly, pAUR123 (TaKaRa) was digested with KpnI and XbaI, and the fragment was ligated using a DNA ligation Kit Ver. 2.1 (TaKaRa). pAUR123-OSC1 was obtained. A region from PADH1 to TADH1 in pAUR123-OSC1 was subjected to PCR using KOD-Plus-DNA polymerase (TOYOBO) in which primers AUR123-F (GGATGATCCACTAGTGGATCCTCTAGCTCCCTAACATGTAGGTGG:SEQ ID NO: 5) and AUR123-R (TAATGCAGGGCCGCAGGATCCGTGTGGAAGAACGATTAC-AACAGG:SEQ ID NO: 6) were used. The PCR was carried out at 94° C. for two minutes, followed by (94° C. for 20 seconds→55° C. for 40 seconds→68° C. for 90 seconds)×20 cycles. The samples were further kept warm at 68° C. for two minutes. Furthermore, a region in pYES3/CT (Invitrogen) excluding from the first nucleotide to the 960th nucleotide (from PGAL1 to CYC1TT) was subjected to PCR using KOD-Plus-DNA polymerase (TOYOBO) in the same manner as mentioned above in which primers YES3-F (TGCGGC-CCTGCATTAATGAATCGGCCAACG:SEQ ID NO: 7) and YES3-R (ACTAGTGGATCATCCCCACGCGCCCTGTAG: SEQ ID NO: 8) were used. Both PCR products thus obtained were linked by using an In-Fusion Dry-Down PCR Cloning Kit (Clontech) to obtain pYES3-ADH-OSC1, yeast expression vector for *Lotus* OSC1.

Example 16

Construction of Yeast Expression Vector pESC-LjCPR1 Comprising *Lotus* Cytochrome P450 Reductase Searching through a *Lotus* EST database (provided by Kazusa DNA Research Institute), nucleic acid sequences having 70% or more homology with *Arabidopsis* cytochrome P450 reductase at an amino acid level were selected. EST clones which presumably comprised a full-length coding region (accession no. AV778635) were obtained from Kazusa DNA Research Institute, and DNA sequences were determined with the use of ABI PRISM 3100 Genetic Analyzer (hereinafter referred to as LjCPR1). Using LjCPR1-introduced plasmids (pBluescript SK (−)) as templates, and using primers CPR-F (Not) (GGGCGGCCGCACTAGTATC-GATGGAAGAATCAAGCTCCATGAAG:SEQ ID NO: 9) and CPR-R (Pac) (TTAATTAATCACCATACATCACG-CAAATAC:SEQ ID NO: 10), PCR was carried out with the use of KOD-Plus-DNA polymerase (TOYOBO) at 94° C. for two minutes, followed by (94° C. for 20 seconds→60° C. for 40 seconds→68° C. for 120 seconds)×15 cycles, and the sample was then kept warm at 68° C. for two minutes. The PCR products thus obtained were ligated with pT7Blue T-vectors (Novagen) using TAget Clone-Plus-(TOYOBO). After confirming nucleotide sequences thereof, they were digested with NotI and PacI while yeast expression vector pESC-LEU (Stratagene) was also digested with NotI and PacI. Thereafter, both were ligated using a DNA ligation Kit Ver. 2.1 (TaKaRa) to obtain yeast expression vectors pESC-LjCPR1 for LjCPR1.

Example 17

Construction of Co-Expression Vector pELC88BN for *G. uralensis*-Derived Oxidase (CYP88D6) at Position 11 of β-Amyrin and LjCPR1 in Yeast Firstly, a gene (GenBank accession no. AB433179) encoding oxidase (CYP88D6) at the position 11 of β-amyrin, which had been previously isolated from *G. uralensis* by the present inventors, was cloned to a yeast expression vector pESC-LEU (Stratagene) by the following method.

Using cDNA encoding CYP88D6 cloned to a pENTR™/ D-TOPO (registered trademark) entry vector as a template, and using primers of both of 88S1 (CGCCGGATCCAC-CATGGAAGTACATTGGGTTTGCATGTCC:SEQ ID NO: 11) and 88AS4 Xba (GCCCTCTAGACTAAGCACAT-GAAACCTTTATCACCTTAGC:SEQ ID NO: 12), PCR was carried out with the use of KOD-Plus-(TOYOBO) at 94° C. for two minutes, followed by (94° C. for 15 seconds→62° C. for 40 seconds→68° C. for 90 seconds)×25 cycles. Thereby, a DNA fragment comprising CYP88D6 cDNA was ampli-fied. The PCR solution was subjected to electrophoresis, the amplified fragment of about 1.5 kb was purified with the use of Wizard SV Gel and PCR Clean-up System (Promega) and digested with the restriction enzymes BamHI and XbaI. The reaction product was purified by using Wizard SV Gel and PCR Clean-up System (Promega). On the other hand, pESC-LEU (Stratagene) was digested with restriction enzymes BamHI and NheI. These were ligated by using DNA ligation Kit Ver2.1 (TaKaRa) to obtain a CYP88D6 yeast expression vector pESC-CYP88D6.

Next, by the method described in Example 16, a DNA fragment comprising cDNA of LjCPR1 was prepared by using the restriction enzymes NotI and PacI. The obtained DNA fragment was introduced into pESC-CYP88D6 that had been digested with restriction enzyme NotI and PacI by using DNA ligation Kit Ver2.1 (TaKaRa). Thus, a co-expression vector pELC88BN of CYP88D6 and LjCPR1 in yeast was obtained.

Example 18

Construction of Vector for Expressing GuCYP72.1 in Yeast

A plasmid (an entry clone) comprising the polynucleotide shown in SEQ ID NO: 3 produced in Example 8 and a destination vector pYES-DEST™ 52 (Invitrogen) were mixed with each other, and a DNA fragment shown in SEQ ID NO: 3 was transferred to pYES-DEST™ 52 by a nucleotide sequence-specific recombination reaction (GATEWAY™ attL×attR reaction) by using Gateway LR Clonase II Enzyme Mix (Invitrogen), thereby a yeast expression vector pDEST52-GuCYP72.1 for the gene shown in SEQ ID NO: 3 was obtained.

Example 19

Production of Transformed Yeast

Transformation of a yeast strain BJ2168 (Nippon Gene) (MATa prc1-407 prb1-1122 pep4-3 leu2 trp1 ura3-52 gal2) was carried out using Frozen-EZ Yeast Transformation II (Zymo Research). Firstly, the yeast strain BJ2168 was transformed with pYES3-ADH-OSC1. Next, the obtained transformed yeast was transformed with pESC-LjCPR1 and pELC88BN, respectively. Furthermore, the two kinds of yeast strains thus obtained were transformed with pDEST52-GuCYP72.1 or pYES2 (Invitrogen) which corresponds to the empty vector.

Example 20

Confirmation of Product in Transformed Yeast (pYES3-ADH-OSC1, pESC-LjCPR1, and pDEST52-GuCYP72.1)

Yeast containing three vectors of pYES3-ADH-OSC1 (*Lotus* β-amyrin synthase expression vector), pESC-LjCPR1 (*Lotus* cytochrome P450 reductase expression vector), and pDEST52-GuCYP72.1 (expression vector of *G. uralensis*-derived oxidase at the position 30 of β-amyrin GuCYP72.1) was cultured in 400 ml of SC-Trp/Leu/Ura medium at 28° C. while shaking at 135 rpm for two days. The yeast thus cultured was collected by centrifugation at 3000 g for 10 minutes, suspended in 400 ml of SC-Trp/Leu/Ura-glucose medium containing galactose (20 mg/ml) and hemin chloride (13 μg/ml), and then cultured at 28° C. while shaking at 135 rpm for two days. Then, the yeast was collected by centrifugation and the obtained pellets were lyophilized. Then, 5 ml of ethyl acetate was added to the obtained sample and mixed, followed by collecting an ethyl acetate extract. This procedure was repeated three times. The ethyl acetate extract was concentrated under reduced pressure. Control yeast containing three vectors of pYES3-ADH-OSC1, pESC-LjCPR1, and pYES2 (empty vector) was similarly cultured and subjected to extraction. As in the method described in Example 14, a solvent was removed by drying from the ethyl acetate part, and subsequently, N-methyl-N-(trimethylsilyl)trifluoroacetamide was added thereto. The mixture was heated at 80° C. for 30 minutes to be derivatized into trimethylsilyl ether, thereby a sample for a GC-MS analysis was provided. Identity of the converted products was determined by comparison with respect to the GC retention time and the MS spectra by using a substrate triterpene prepared in Example 12 as an authentic sample.

Figure 5:
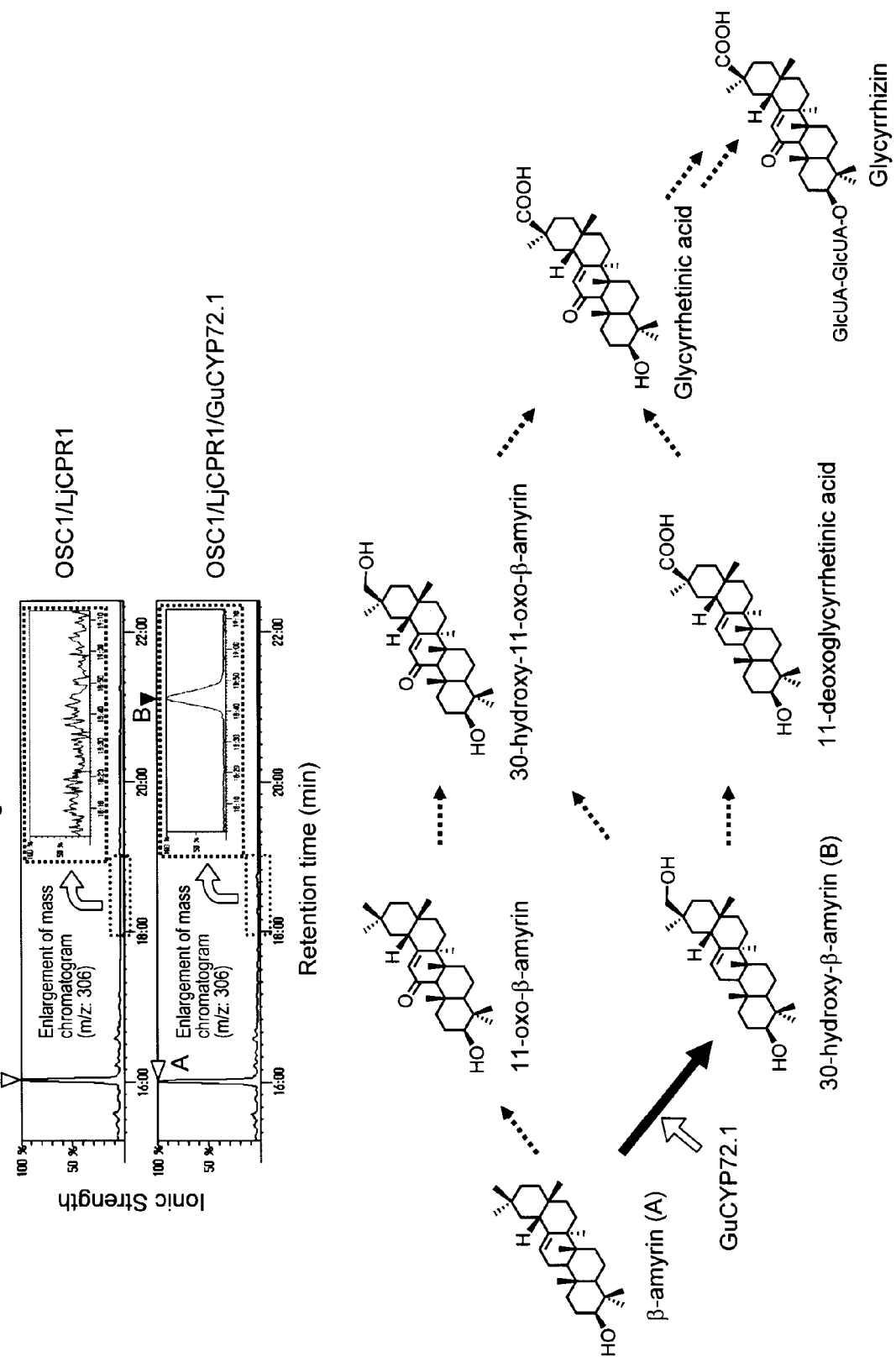
FIG. 5 shows a result of detection of a converted product of β-amyrin by polypeptide of the present invention, and also shows the position of catalysis by the polypeptide in a presumable biosynthetic pathway from β-amyrin to glycyrrhizin.

From the extract of the yeast containing three vectors of pYES3-ADH-OSC1, pESC-LjCPR1, and pDEST52-GuCYP72.1 (FIG. 5: a GC chart represented by OSC1/LjCPR1/GuCYP72.1), 30-hydroxy-β-amyrin (black arrow B) was detected in addition to β-amyrin (void arrow A). On the other hand, from the extract of the yeast containing three vectors of pYES3-ADH-OSC1, pESC-LjCPR1, and pYES2 in a control experiment (FIG. 5: a GC chart represented by OSC1/LjCPR1), only β-amyrin (void arrow A) was detected and 30-hydroxy-β-amyrin was not detected.

From the above-mentioned results, it was revealed that an enzyme encoded by the gene (GuCYP72.1) of the present invention converted methylene carbon at the position 30 of β-amyrin generated in yeast expressing β-amyrin synthase (OSC1) into a hydroxyl group so as to produce 30-hydroxy-β-amyrin.

Example 21

Identification of 30-Hydroxy-β-Amyrin by NMR

Figure 6:
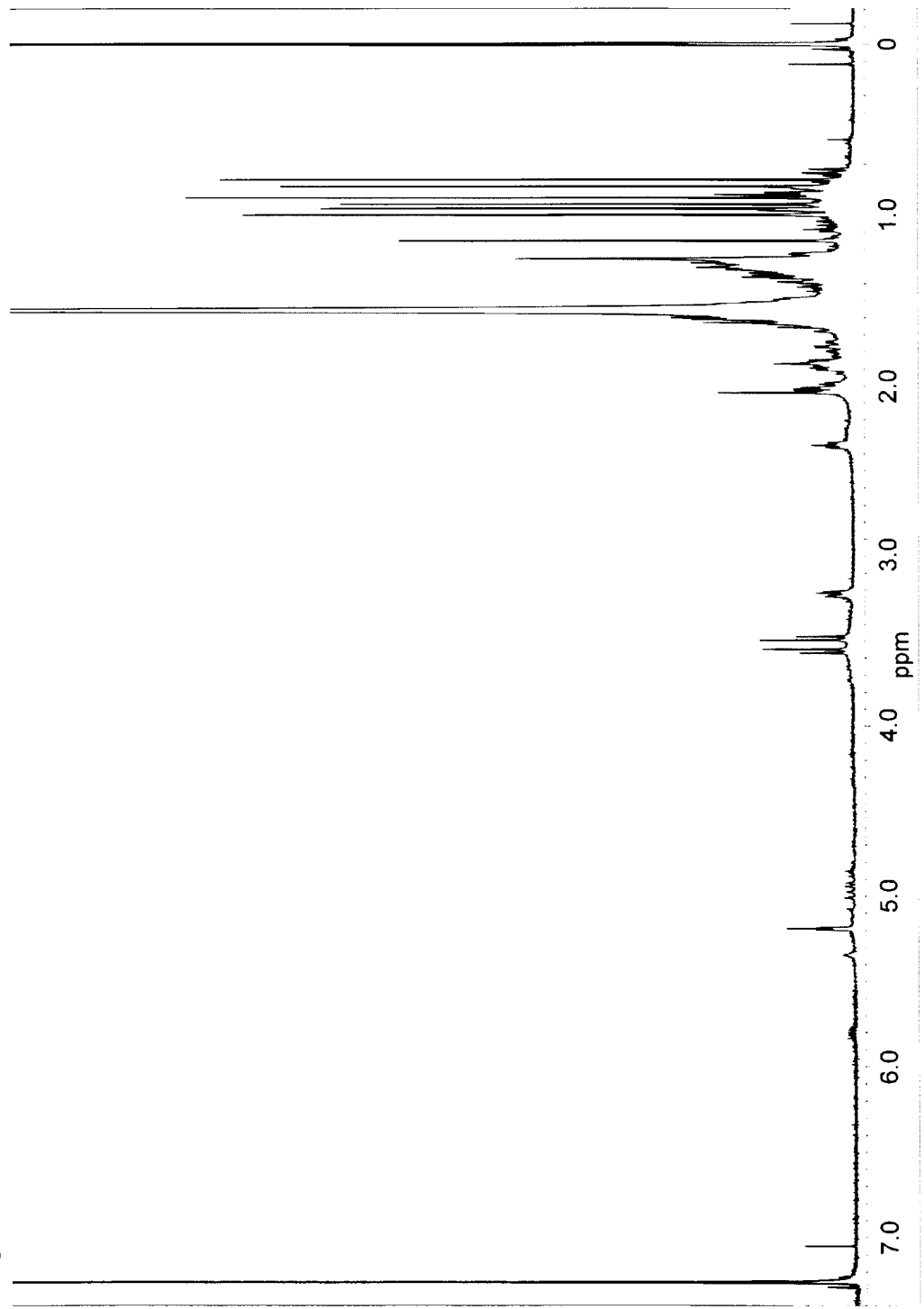
FIG. 6 shows results of measurement of 30-hydroxy-β-amyrin by NMR.

Yeast containing three vectors of pYES3-ADH-OSC1, pESC-LjCPR1, and pDEST52-GuCYP72.1 was cultured in 400 ml of SC-Trp/Leu/Ura medium (12 containers, a total of 4.8 L) at 28° C. while shaking at 125 rpm for two days. The yeast thus cultured was collected by centrifugation at 3000 g for 10 minutes and suspended in 400 ml of SC-Trp/Leu/Ura-glucose medium (12 containers, a total of 4.8 L) containing galactose (20 mg/ml) and hemin chloride (13 µg/ml), which was then cultured at 28° C. while shaking at 125 rpm for two days. The yeast was collected by the centrifugation and the obtained pellets were lyophilized. To the yeast thus lyophilized, 100 ml of chloroform was added and mixed, followed by collecting a chloroform extract. This procedure was repeated three times. The chloroform extract was concentrated under reduced pressure. To the chloroform extract to which 100 ml of water had been added, 100 ml ethyl acetate was added and mixed to collect an ethyl acetate extract. This procedure was repeated three times. The ethyl acetate extract was dried over anhydrous magnesium sulfate, and then concentrated under reduced pressure. Thereafter, the ethyl acetate extract was fractionated by silica gel chromatography. For silica gel chromatography, Wako gel C-200 (Wako Pure Chemical Industries, Ltd.) with 2.8×40 cm was used. A solvent containing hexane:ethyl acetate at 1:1 was allowed to flow, and an eluate was fractionated into 7 ml of fractions. Fractions 41 to 51 were gathered and the solvent was removed, and then the gathered fractions were subjected to a silica gel TLC plate LK6F (Whatman) with 20×20 cm. After the plate was developed with hexane:ethyl acetate (1:1), a silica gel exhibiting the same Rf value as that of 30-hydroxy-β-amyrin was scratched off and eluted with chloroform. After removing the solvent, a remaining substance was dissolved in deuterated chloroform and $^1$H-NMR spectrum was measured by using a NMR (500 MHz) manufactured by JEOL Ltd. The $^1$H-NMR spectrum of this fraction completely corresponded to 30-hydroxy-β-amyrin as the authentic sample prepared in Example 3 (CDCl3, 500 MHz: δ 0.79 (3H, s), 0.83 (3H, s), 0.90 (3H, s), 0.94 (3H, s), 0.96 (3H, s), 1.00 (3H, s), 1.15 (3H, s), 3.22 (1H, dd, J=4.6, 11.5 Hz), 3.48 (1H, d, J=10.9 Hz), 3.56 (1H, d, J=10.9 Hz), 5.19 (1H, t, J=3.4 Hz)). The result is shown in FIG. 6.

Example 22

Confirmation of Product in Transformed Yeast (pYES3-ADH-OSC1, pELC88BN, and pDEST52-GuCYP72.1)

Yeast containing three vectors of pYES3-ADH-OSC1 (*Lotus* β-amyrin synthase expression vector), pELC88BN (a co-expression vector of oxidase CYP88D6 at the position 11 of β-amyrin derived from *G. uralensis* and cytochrome P450 reductase LjCPR1 derived from *Lotus*), and pDEST52-GuCYP72.1 (an expression vector of oxidase GuCYP72.1 at the position 30 of β-amyrin derived from *G. uralensis*) was cultured by the method shown in Example 20, and the cultured product was subjected to extraction. Identity of the converted products was determined by comparison with respect to the GC retention time and the MS spectra by using a substrate triterpene prepared in Example 12 as an authentic sample.

Figure 7:
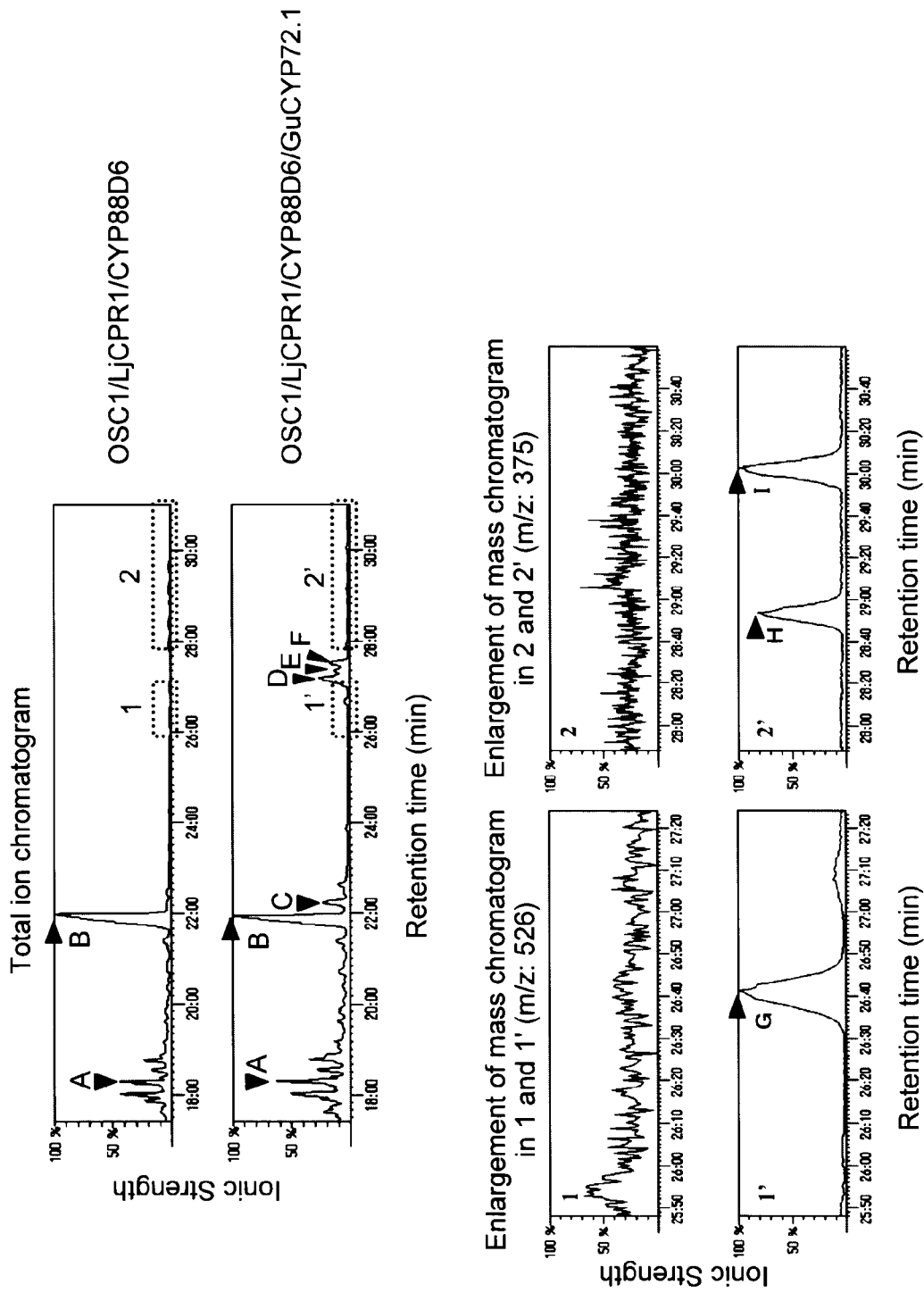
FIG. 7 shows the result of detecting a converted product of β-amyrin by a polypeptide of the present invention (GuCYP72.1) and oxidase at position 11 of β-amyrin (CYP88D6).

As a result, from the extract of the yeast containing three vectors of pYES3-ADH-OSC1, pELC88BN, and pDEST52-GuCYP72.1 (FIG. 7: GC chart represented by OSC1/LjCPR1/CYP88D6/GuCYP72.1), in addition to β-amyrin (FIG. 7: peak A, FIG. 8: compound A) and 11-oxo-β-amyrin (FIG. 7: peak B, FIG. 8: compound B), 30-hydroxy-β-amyrin (FIG. 7: peak C, FIG. 8: compound C), 30-hydroxy-11-oxo-β-amyrin (FIG. 7: peak D, FIG. 8: compound D), glycyrrhetinic acid (FIG. 7: peak H, FIG. 8: compound H) and 20-epi-glycyrrhetinic acid (FIG. 7: peak I) were detected. Furthermore, although a structure was not determined, from the mass spectrum pattern, peaks E and F that were presumed to be a hydroxylated compound of 11-oxo-β-amyrin as well as peak G that was presumed to be an aldehyde at the position 30, which was a further oxidized compound D, were also detected.

On the other hand, from the extract of the yeast having only two vectors of pYES3-ADH-OSC1 and pELC88BN as control (FIG. 7: GC chart represented by OSC1/LjCPR1/CYP88D6), β-amyrin (peak A) and 11-oxo-β-amyrin (peak B) were detected, but 30-hydroxy-β-amyrin, 30-hydroxy-11-oxo-β-amyrin, glycyrrhetinic acid and 20-epi-glycyrrhetinic acid were not detected.

From the above-mentioned results, it was revealed that an enzyme encoded by the gene (GuCYP72.1) of the present invention converted methylene carbon at the position 30 of 11-oxo-β-amyrin generated in yeast co-expressing β-amyrin synthase (OSC1) and oxidase (CYP88D6) at the position 11 of β-amyrin into a carboxyl group, and thus glycyrrhetinic acid as a precursor (sapogenin) of glycyrrhizin and the isomer thereof, 20-epi-glycyrrhetinic acid, can be produced.

Example 23

Isolation of Polypeptide of the Present Invention from *G. glabra*

From *G. glabra*, a homologous gene (GgCYP72.1) presumed to have a function equivalent to the gene shown in SEQ ID NO: 3 was isolated by a RT-PCR method.

Total RNA was prepared from stolons of *G. glabra* provided by Research Center for Medicinal Plant Resources, Hokkaido Division (Nayoro city, Hokkaido), of National Institute of Biomedical Innovation. The obtained total RNA (1 μg) was subjected to first strand cDNA synthesis using SMART RACE cDNA amplification kit (Clontech) according to the attached protocol. PCR was carried out at an annealing temperature of 55° C. for 30 cycles using nucleotides shown in SEQ ID NOs: 1 and 2 as primers, and using Pfu-Turbo DNA Polymerase (Stratagene). The DNA fragment amplified by the PCR was cloned to pENTR™/D-TOPO (an entry vector), and nucleotide sequences of the amplified DNA fragments of independent four clones thus obtained were determined. The sequence thus obtained is SEQ ID NO: 13, and a polypeptide sequence predicted therefrom is SEQ ID NO: 14. The amino acid sequence shown in SEQ ID NO: 14 had a 98.5% identity with the amino acid sequences shown in SEQ ID NO: 4.

Example 24

Addition Experiment of 30-Hydroxy-11-Oxo-β-Amyrin to GuCYP72.1 Expression Yeast

Firstly, a yeast strain, BJ2168 (Nippon Gene), was transformed with pESC-LjCPR1. Next, the obtained transformed yeast was transformed with pDEST52-GuCYP72.1 or pYES2 (Invitrogen) corresponding to an empty vector.

The respective transformed yeast strains were cultured in 100 ml of SC-Leu/Ura medium at 28° C. while shaking at 135 rpm for two days. The yeast thus cultured was collected by centrifugation at 3000 g for 10 minutes, suspended in 100 ml of SC-Leu/Ura-glucose medium containing galactose (20 mg/ml), hemin chloride (13 μg/ml), and 2 μM of 30-hydroxy-11-oxo-β-amyrin, and then cultured at 28° C. at 135 rpm for two days. To the yeast culture solution, ethyl acetate was added and mixed therewith, followed by collecting an ethyl acetate extract. A solvent was removed by drying from the ethyl acetate part, to which N-methyl-N-(trimethylsilyl)trifluoroacetamide was added. The mixture was heated at 80° C. for 30 minutes to be derivatized into a trimethylsilyl ether, and thus a sample for a GC-MS analysis was provided.

Figure 8:
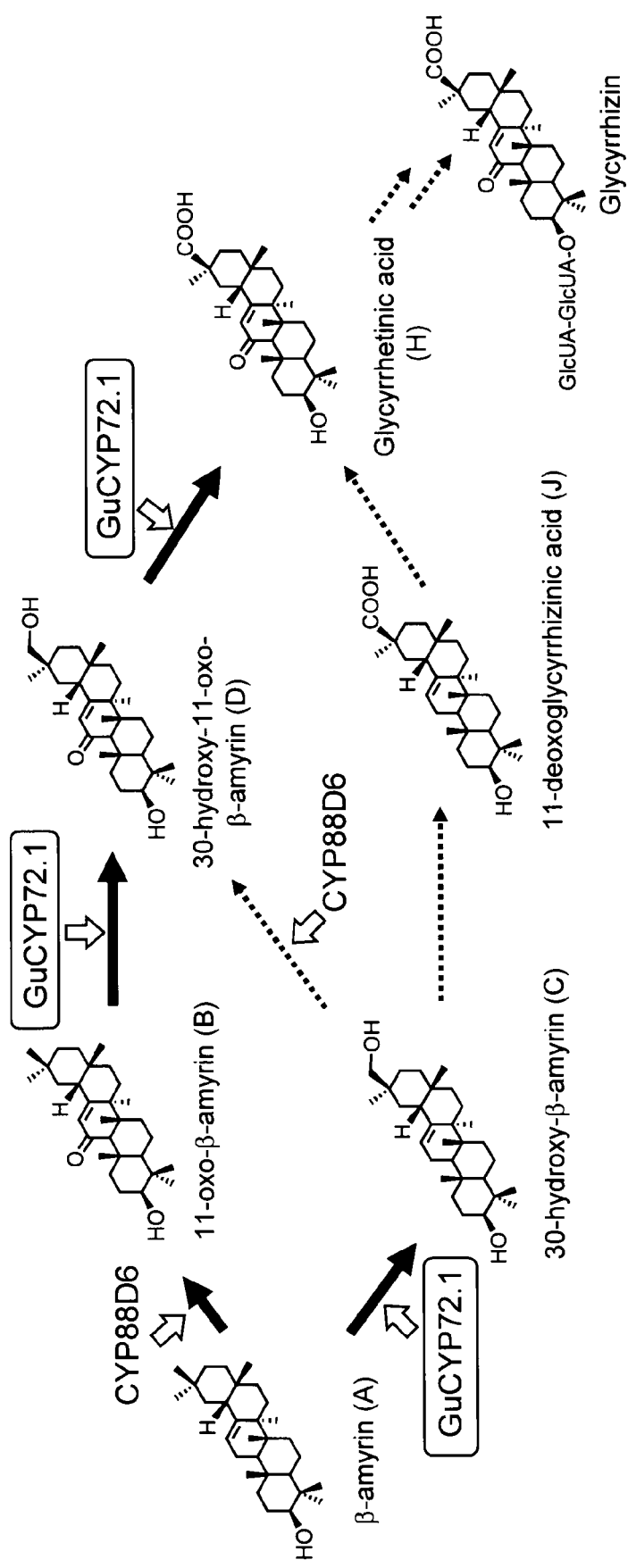
FIG. 8 shows a presumable biosynthetic pathway from β-amyrin to glycyrrhizin by the polypeptide (GuCYP72.1) and the enzyme that oxidizes β-amyrin at the position 11 (oxidase at the position 11 of β-amyrin) (CYP88D6) and the positions of catalysis by the polypeptides and the enzymes in accordance with the present invention.
Figure 9:
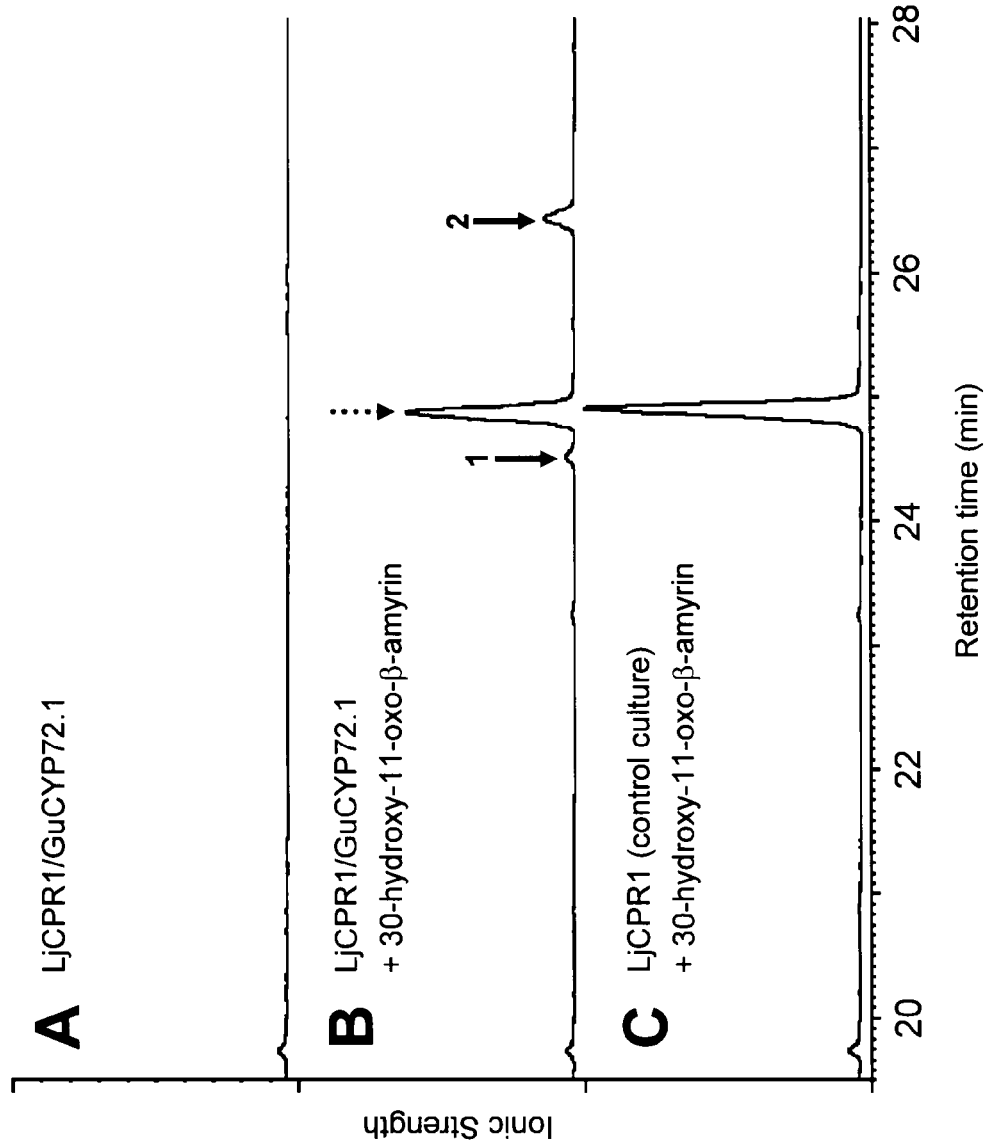
FIG. 9 shows production of glycyrrhetinic acid by the addition of 30-hydroxy-11-oxo-β-amyrin to yeast expressing polypeptide (GuCYP72.1) in accordance with the present invention.

From the extract when the yeast containing two vectors of pESC-LjCPR1 and pDEST52-GuCYP72.1 was cultured in a medium containing 30-hydroxy-11-oxo-β-amyrin (FIG. 9, GC chart B), glycyrrhetinic acid (peak 2; compound H in FIG. 8) was detected in addition to 30-hydroxy-11-oxo-β-amyrin (a dotted-line arrow; compound D in FIG. 8). Furthermore, although a structure was not determined, peak 1 was also detected from the mass spectrum pattern, which was presumed to be an aldehyde at the position 30. On the other hand, when the same yeast strain was cultured in a medium without containing 30-hydroxy-11-oxo-β-amyrin (FIG. 9, GC chart A), none of such peaks was detected.

Furthermore, when yeast containing two vectors of pESC-LjCPR1 and pYES2 (an empty vector) was cultured in a medium containing 30-hydroxy-11-oxo-β-amyrin (FIG. 9, GC chart C), only 30-hydroxy-11-oxo-β-amyrin (a dotted-line arrow) was detected and glycyrrhetinic acid of peak 2 was not detected.

Example 25

Identification of Glycyrrhetinic Acid by NMR

Figure 10:
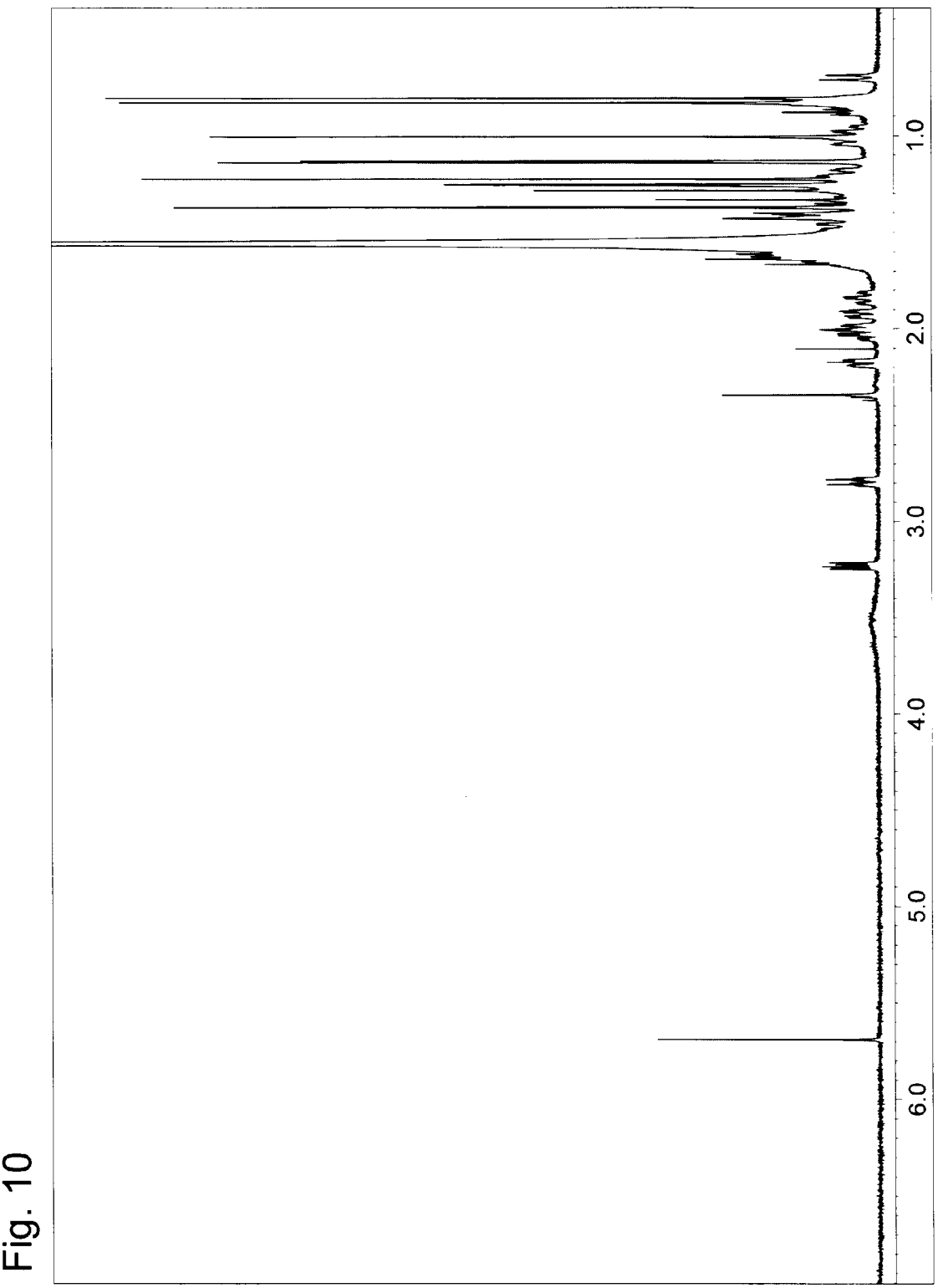
FIG. 10 shows measurement result of glycyrrhetinic acid by NMR.

Yeast containing two vectors of pESC-LjCPR1 and pDEST52-GuCYP72.1 and a solution (0.9 μg/ml) of 30-hydroxy-β-amyrin in ethanol were added to 400 ml of SC-Leu/Ura medium (12 containers, a total of 4.8 L) and the mixture was then cultured at 28° C. while shaking at 125 rpm for two days. The yeast thus cultured was collected by centrifugation at 3000 g for 10 minutes, and suspended in 400 ml of SC-/Leu/Ura-glucose medium (12 containers, a total of 4.8 L) containing galactose (20 mg/ml) and hemin chloride (13 μg/ml), which was then cultured at 28° C. while shaking at 125 rpm for two days. After 400 ml of ethyl acetate was added to the culture solution and mixed, an ethyl acetate extract was collected. This procedure was repeated three times. The ethyl acetate extract was concentrated under reduced pressure, and then fractionated by silica gel chromatography. The silica gel chromatography was carried out using silica gel 60N (Kanto Kagaku) with 3.0×15 cm, hexane:ethyl acetate (1:1) was allowed to flow, and an eluate was fractionated into 50 ml-fractions. Thereafter, fractions Nos. 5 to 7 were collected and the solvent was removed. The residue was dissolved in methanol, and the solution was filtered through a membrane filter (Advantec Toyo) to obtain a sample for the reverse phase HPLC and preparative isolation was carried out (preparative isolation conditions: column, PEGASIL ODS, 25 cm×6 mm i.d. (Senshu Scientific); mobile phase, acetonitrile (0.1% acetic acid); flow rate, 1.5 ml/min; UV detector 248 nm). Preparative isolation was carried out every 30 seconds from 5 min to 10 min, and fractions Nos. 3 and 4 were collected and the solvent was removed. The residue was subjected to a silica gel TLC plate (Merck, Silica gel 60 $F_{254}$, 20×10 cm). After the plate was developed with hexane:ethyl acetate (1:1, 0.5% acetic acid), a silica gel exhibiting the same Rf value as glycyrrhetinic acid was scratched off and eluted with ethyl acetate:chloroform (1:1). After removing the solvent, a remaining substance was dissolved in deuterated chloroform and $^1$H-NMR spectrum was measured by using a (500 MHz) NMR manufactured by JEOL Ltd. The $^1$H-NMR spectrum of this fraction completely corresponded to glycyrrhetinic acid as an authentic sample (CDCl3, 500 MHz: δ 0.81 (3H, s), 0.83 (3H, s), 1.01 (3H, s), 1.13 (3H, s), 1.14 (3H, s), 1.23 (3H, s), 1.37 (3H, s), 2.34 (1H, s), 3.23 (1H, dd, J=5.4, 10.9 Hz), 5.69 (1H, s)). The result is shown in FIG. 10.

Example 26

Search of GuCYP72.1 Homologous Gene of *Medicago truncatula*

In order to verify that an enzyme having an activity of oxidizing carbon at the position 30 of oleanane-type triterpene of the present invention is not limited to the genus *Glycyrrhiza* but exists in all the family Fabaceae, the following experiments were carried out by using *Medicago truncatula*. *Medicago truncatula* is a plant belonging to the genus *Medicago*, which belongs to a plant in the subfamily Faboideae in the family Fabaceae like the genus *Glycyrrhiza* and which is phylogenetically distant from the genus *Glycyrrhiza*.

*Medicago truncatula*, a plant belonging to the genus *Medicago* of the family Fabaceae, is known to produce a plurality of triterpenoid saponins having β-amyrin in the base skeleton, similar to glycyrrhizin. In *Medicago truncatula*, a homologous gene that is expected to have a function similar to that of GuCYP72.1 gene shown in SEQ ID NO: 3 was searched. With the homology search, from the TC (Tentative consensus=a longer cDNA sequence predicted from the overlap of EST clones) sequences registered in *Medicago truncatula* public EST database DFCI *Medicago* Gene Index Release 8.0, the polynucleotide sequence, TC113088, showing 83% identity of nucleotide sequence with a full length coding region GuCYP72.1, was found.

Example 27

Isolation of GuCYP72.1 Homologous Gene of *Medicago truncatula*

*Medicago truncatula*, ecotype R108-1 was cultivated in an artificial climate chamber (23° C., day length: 16 hours). Total RNA was prepared from leaf, stem, and root of a plant on week 4 after budding. The obtained total RNA (1 μg) was subjected to a first strand cDNA synthesis using SMART RACE cDNA amplification kit (Clontech) according to the attached protocol.

PCR (34 cycles, using KOD plus ver. 2 polymerase (TOYOBO)) was carried out at an annealing temperature of 54° C. using 2 μl each of three kinds of first strand cDNAs as templates and using oligo DNAs for the sites corresponding to the N-terminal and the C-terminal of polypeptides (524 amino acids) presumed from TC113088, that is, SEQ ID NO: 19 (caccATGGAAGTGTTTATGTTTCCCACAGG) and SEQ ID NO: 20 (TTACAGTTTATGCAAAATGATGCTTGCA) as primers. Note here that four nucleotides (cacc) were artificially added to 5'-terminal of the primer of SEQ ID NO: 19 because they were necessary for cloning to pENTR™/D-TOPO (registered trademark) entry vector (Invitrogen). As a result of PCR, when any of the first strand cDNAs was used as a template, an about 1.6-kb DNA fragment was amplified at the same level. The DNA fragment amplified from the first strand cDNA derived from the stem was cloned to pENTR™/D-TOPO entry vector, and the polynucleotide sequences of the independent four clones thus obtained were determined. The sequence thus obtained is SEQ ID NO: 17, and a polypeptide sequence predicted therefrom is SEQ ID NO: 18. The SEQ ID NO: 18 had 75.5% identity with the amino acid sequence shown in SEQ ID NO: 4. Hereinafter, P450 molecular species shown in SEQ ID NO: 18 is referred to as MtCYP72.1.

Example 28

Construction of Yeast Co-Expression Vector pELC-MtCYP72.1 of LjCPR1 and MtCYP72.1 pESC-LjCPR1 constructed in Example 16 was converted into an expression vector corresponding to Gateway technology by the following method.

A pAM-PAT-GW vector (provided from Dr. Bekir Ulker and Dr. Imre E. Somssich of Max Planck Institute) was double-digested with restriction enzymes XhoI and SpeI, and a DNA fragment comprising Gateway conversion cassette (Invitrogen) was cut out. The obtained DNA fragment was connected to larger one of the two fragments obtained by double-digesting pESC-LjCPR1 with SalI and NheI, and thus pELC-MCS2-GW was constructed. For constructing pELC-MCS2-GW, *Escherichia coli* DB3.1 strain (Invitrogen) was used.

Next, a plasmid (entry clone) having a polynucleotide shown in SEQ ID NO: 17, which had been produced in Example 27, was mixed with pELC-MCS2-GW. Then, a DNA fragment shown in SEQ ID NO: 17 was transferred to pELC-MCS2-GW by nucleotide sequence-specific recombinant reaction (attLxattR reaction) using Gateway LR Clonase II Enzyme Mix (Invitrogen), and thereby a co-expression vector pELC-MtCYP72.1 of LjCPR1 and a gene shown in SEQ ID NO: 17 was obtained.

Example 29

Production of Transformed Yeast Co-Expressing OSC1 and MtCYP72.1

Transformation of an INVSc1 strain (Invitrogen) (MATa his3D1 leu2 trp1-289 ura3-52 MATAlpha his3D1 leu2 trp1-289 ura3-52) was carried out by using Frozen-EZ Yeast Transformation II (Zymo Research). Firstly, a yeast INVSc1 strain was transformed with pYES3-ADH-OSC1. Subsequently, the obtained transformed yeast was transformed with pELC-MtCYP72.1 or pESC-LjCPR1 as a control.

Example 30

Confirmation of Product in Transformed Yeast (pYES3-ADH-OSC1, pELC-MtCYP72.1)

Yeast containing two vectors of pYES3-ADH-OSC1 and pELC-MtCYP72.1 was cultured in 5 ml of SC-Trp/Leu medium at 30° C. at 135 rpm for one day. The yeast thus cultured was collected by centrifugation at 3000 g for 10 minutes and suspended in 10 ml of SC-Trp/Leu-glucose medium containing galactose (20 mg/ml) and hemin chloride (13 μg/ml), and then cultured at 30° C. at 135 rpm for two days. To the yeast culture solution, 5 ml of ethyl acetate was added and mixed, followed by collecting an ethyl acetate extract. This procedure was repeated three times. The ethyl acetate extract was concentrated under reduced pressure. Yeast containing two vectors of pYES3-ADH-OSC1 and pESC-LjCPR1 was cultured and subjected to extraction similarly. As in the method described in Example 14, a solvent was removed by drying from the ethyl acetate part. Subsequently, N-methyl-N-(trimethylsilyl)trifluoroacetamide was added thereto and the mixture was heated at 80° C. for 30 minutes to be derivatized into trimethylsilyl ether, and thereby a sample for a GC-MS analysis was provided. Identification of the converted products was determined by comparison with respect to the GC retention time and the MS spectra by using triterpenoid prepared in Example 12 as an authentic sample.

Figure 11:
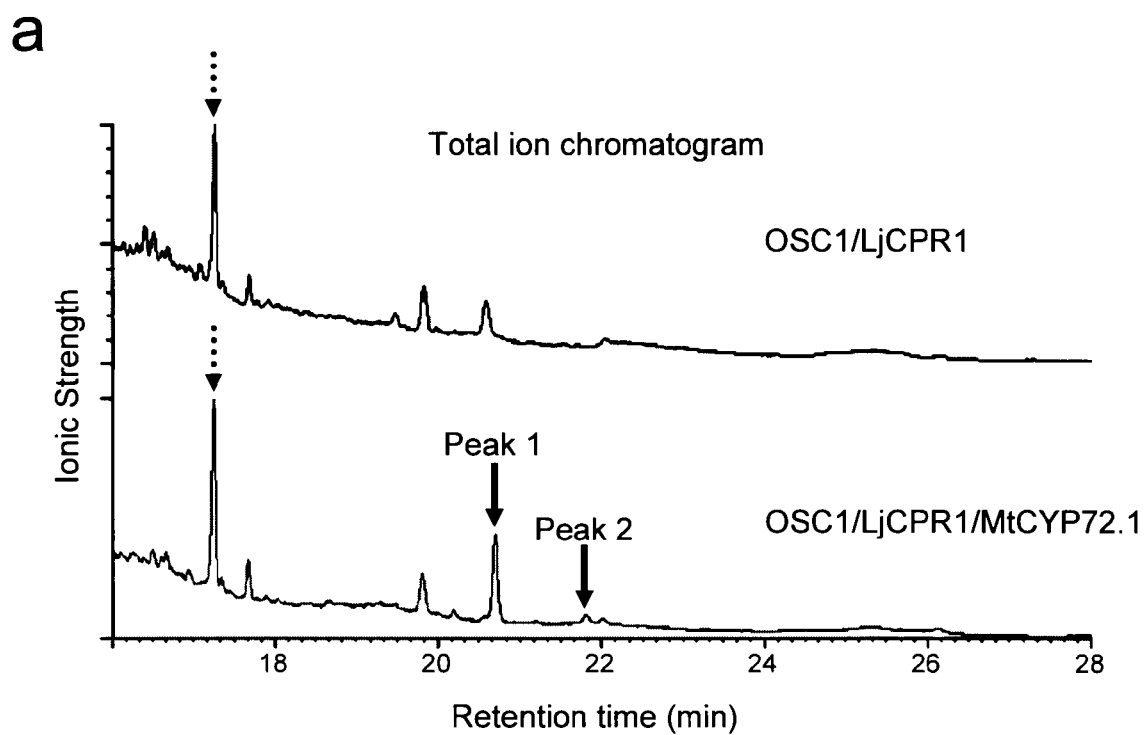
FIG. 11 shows detection results of a converted product of β-amyrin by polypeptide (MtCYP72.1) in accordance with the present invention.
Figure 11:
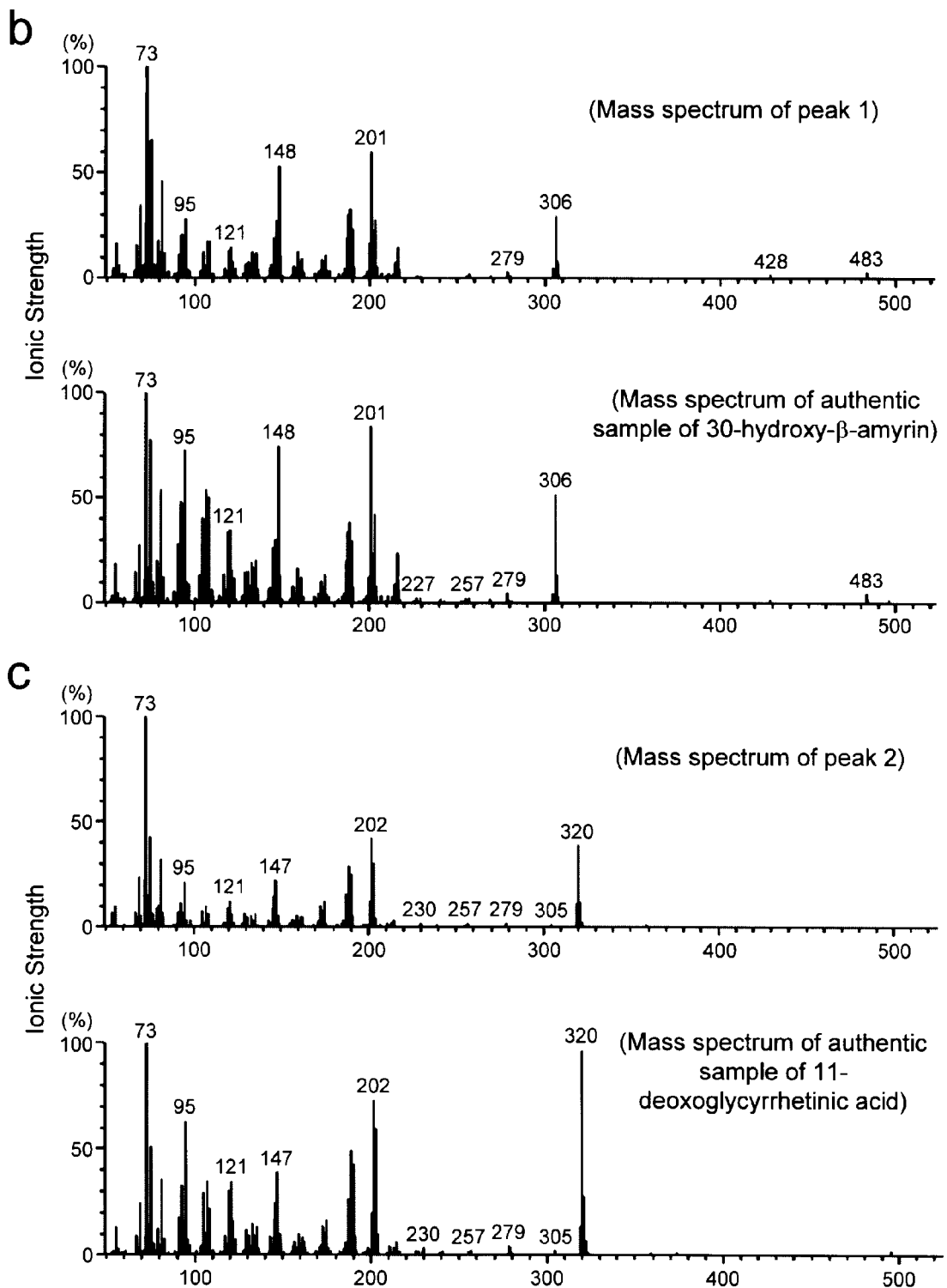

From the extract of the yeast containing two vectors of pYES3-ADH-OSC1 and pELC-MtCYP72.1 (FIG. 11a, GC chart represented by OSC1/LjCPR1/MtCYP72.1), specific two peaks (peaks 1 and 2) were detected in addition to β-amyrin (a dotted-line arrow; compound A in FIG. 8). Among them, the mass spectrum of peak 1 corresponds well to that of 30-hydroxy-β-amyrin (compound C in FIG. 8) (FIG. 11b). Furthermore, the mass spectrum of peak 2 corresponds well to that of 11-deoxoglycyrrhetinic acid (compound J in FIG. 8) (FIG. 11c). Thus, it has been revealed that peak 1 corresponds to 30-hydroxy-β-amyrin, and peak 2 corresponds to 11-deoxoglycyrrhetinic acid, respectively.

On the other hand, from the extract of the yeast containing two vectors of pYES3-ADH-OSC1 and pESC-LjCPR1 (FIG. 11a, GC chart represented by OSC1/LjCPR1), β-amyrin (a dotted-line arrow) was detected but 30-hydroxy-β-amyrin (peak 1) and 11-deoxoglycyrrhetinic acid (peak 2) were not detected.

From the above-mentioned results, it has been revealed that MtCYP72.1 converts methylene carbon at the position 30 of β-amyrin (compound A in FIG. 8) generated in yeast that expresses β-amyrin synthase (OSC1) into a carboxyl group, and thus 11-deoxoglycyrrhetinic acid (compound J in FIG. 8) can be produced.

The invention claimed is:

1. An isolated cDNA polynucleotide encoding a polypeptide having an activity of oxidizing carbon at a position 30 of an oleanane-type triterpene, wherein the isolated cDNA polynucleotide comprises:
   a nucleotide sequence of SEQ ID NO:3, SEQ ID NO:13, or SEQ ID NO:17.

2. The isolated cDNA polynucleotide according to claim 1, wherein the oleanane-type triterpene is β-amyrin, 11-oxo-β-amyrin, or 30-hydroxy-11-oxo-β-amyrin.

3. A recombinant vector comprising the isolated cDNA polynucleotide according to claim 1.

4. A transformant comprising the isolated cDNA polynucleotide according to claim 1.

5. The transformant according to claim 4, wherein the transformant is a plant in the family Fabaceae.

6. The transformant according to claim 5, wherein the plant in the family Fabaceae is a plant in the subfamily Faboideae.

7. The transformant according to claim 6, wherein the plant in the family Fabaceae is a plant belonging to the genus *Glycyrrhiza* or the genus *Medicago*.

8. The transformant according to claim 7, wherein the plant belonging to the genus *Glycyrrhiza* is *G. uralensis* or *G. glabra*.

9. The transformant according to claim 7, wherein the plant belonging to the genus *Medicago* is *M. truncatula*.

10. The transformant according to claim 4, wherein expression of the isolated cDNA polynucleotide is enhanced.

11. The transformant according to claim 4, wherein expression of the polynucleotide is suppressed.

12. A method for manufacturing a polypeptide, the method comprising:
    culturing or growing the transformant according to claim 4; and
    extracting the polypeptide from the cultured product or the grown product.

13. A method for manufacturing glycyrrhetinic acid and 20-epi-glycyrrhetinic acid, the method comprising allowing the polypeptide encoded by the isolated cDNA polynucleotide according to claim 1 and a polypeptide having an activity of oxidizing carbon at a position 11 of an oleanane-type triterpene to act on an oleanane-type triterpene.

14. An isolated cDNA polynucleotide, comprising a nucleotide sequence of SEQ ID NO:3, SEQ ID NO:13, or SEQ ID NO:17.

15. A recombinant vector comprising the isolated cDNA polynucleotide according to claim 14.

16. A transformant comprising the isolated cDNA polynucleotide according to claim 14.

17. The transformant according to claim 16, wherein the transformant is a plant in the family Fabaceae.

18. The transformant according to claim 17, wherein the plant in the family Fabaceae is a plant in the subfamily Faboideae.

19. The transformant according to claim 18, wherein the plant in the family Fabaceae is a plant belonging to the genus *Glycyrrhiza* or the genus *Medicago*.

20. The transformant according to claim 19, wherein the plant belonging to the genus *Glycyrrhiza* is *G. uralensis* or *G. glabra*.

21. The transformant according to claim 19, wherein the plant belonging to the genus *Medicago* is *M truncatula*.

22. The transformant according to claim 16, wherein expression of the isolated cDNA polynucleotide is enhanced.

23. The transformant according to claim 16, wherein expression of the isolated cDNA polynucleotide is suppressed.

24. A method for manufacturing a polypeptide, the method comprising:
    culturing or growing the transformant according to claim 16; and
    extracting the polypeptide from the cultured product or the grown product.

25. A method for manufacturing glycyrrhetinic acid and 20-epi-glycyrrhetinic acid, the method comprising allowing the polypeptide encoded by the isolated cDNA polypeptide according to claim 14 and a polypeptide having an activity of an oxidizing carbon at a position 11 of an oleanane-type triterpene to act on an oleanane-type triterpene.

* * * * *